(12) United States Patent
Marc

(10) Patent No.: US 9,080,198 B2
(45) Date of Patent: Jul. 14, 2015

(54) GROWTH MEDIUM FOR THE DETECTION OF MICROORGANISMS BY FLUORESCENCE ALLYING A FLUOROGENIC SUBSTRATE AND A PH-SENSITIVE FLUOROPHORE

(75) Inventor: Frederic Marc, Itterswiller (FR)

(73) Assignee: EMD Millipore Corporation, Billerica, MA (US)

( * ) Notice: Subject to any disclaimer, the term of this patent is extended or adjusted under 35 U.S.C. 154(b) by 239 days.

(21) Appl. No.: 13/522,797

(22) PCT Filed: Jan. 19, 2011

(86) PCT No.: PCT/IB2011/050234
§ 371 (c)(1),
(2), (4) Date: Jul. 18, 2012

(87) PCT Pub. No.: WO2011/092610
PCT Pub. Date: Aug. 4, 2011

(65) Prior Publication Data
US 2012/0301916 A1    Nov. 29, 2012

(30) Foreign Application Priority Data

Jan. 27, 2010  (FR) .................................. 10 50529

(51) Int. Cl.
C12Q 1/00        (2006.01)
C12Q 1/04        (2006.01)
(52) U.S. Cl.
CPC ..................................... C12Q 1/045 (2013.01)
(58) Field of Classification Search
None
See application file for complete search history.

(56) References Cited

U.S. PATENT DOCUMENTS 5,861,270 A * 1/1999 Nelis ............................... 435/34
2009/0325220 A1 12/2009 Reed et al.

FOREIGN PATENT DOCUMENTS

| EP | 1679364 A1 | 7/2006 |
| EP | 2107119 A1 | 10/2009 |
| EP | 2256103 | * 1/2010 |
| EP | 2256103 A1 | 12/2010 |
| FR | 2921670 A1 | 4/2009 |
| WO | 02/065122 A1 | 8/2002 |
| WO | 2005/083109 A1 | 9/2005 |
| WO | 2010/128120 A1 | 11/2010 |

OTHER PUBLICATIONS

Grange, J.M., Journal of Clinical Pathology. 1978. 31, 378-381.*
International Search Report and Written Opinion dated Apr. 14, 2011 in corresponding PCT application No. PCT/IB2011/050234.
International Preliminary Report on Patentability mailed Aug. 9, 2012 in corresponding PCT application No. PCT/IB2011/050234.
Journal of Microbiological Methods, vol. 53, No. 1, Apr. 2003, pp. 11-15, "Enzymatic differentiation of Candida parapsilosis from other Candida spp. in a membrane filtration test", Bauters, et al.
ACS Chemical Biology, vol. 3, No. 3, Mar. 2008, pp. 142-155, "Bright Ideas for Chemical Biology", Lavis, et al.
Chem. Commun., 2000, pp. 2323-2324, DOI: 10.1039/b007108k, "A pH sensitive fluorescent cyanine dye for biological applications", Briggs, et al.
Journal of Microbiological Methods, vol. 46, (2001), pp. 261-267, "Potential problems with fluorescein diacetate assays of cell viability when testing natural products for antimicrobial activity", Clarke, et al.
International Journal of Systematic and Evolutionary Microbiology, (2006), vol. 56, pp. 339-342, DOI 10.1099/ijs.0.63966-0, "Methylobacterium adhaesivum sp. nov., a methylotrophic bacterium isolated from drinking water", Gallego, et al.
Journal of Parenterel Science & Technology, Sep.-Oct. 1993, vol. 47, No. 5, pp. 254-257, "The Incubation Period in Sterility Testing", Bathgate, et al.
Microbiology and Molecular Biology Reviews, Sep. 1991, vol. 55, No. 3, pp. 335-348, "Fluorogenic and chromogenic substrates used in bacterial diagnostics", Manafi, et al.

* cited by examiner

Primary Examiner — Irene Marx
(74) Attorney, Agent, or Firm — Nields, Lemack & Frame, LLC

(57) ABSTRACT

The invention relates to a growth medium allying a fluorogenic substrate and a pH-sensitive fluorophore, in particular the combination of 4-methylumbelliferone (4-MU) and derivatives of fluorescein. This growth medium is used for the detection by fluorescence of microorganisms by coupling the fluorescence measurements relating to the pH-sensitive fluorophor and the fluorescence measurements relating to the activation of the fluorogenic substrate(s) by the microorganisms.

3 Claims, 30 Drawing Sheets

Figure 2:
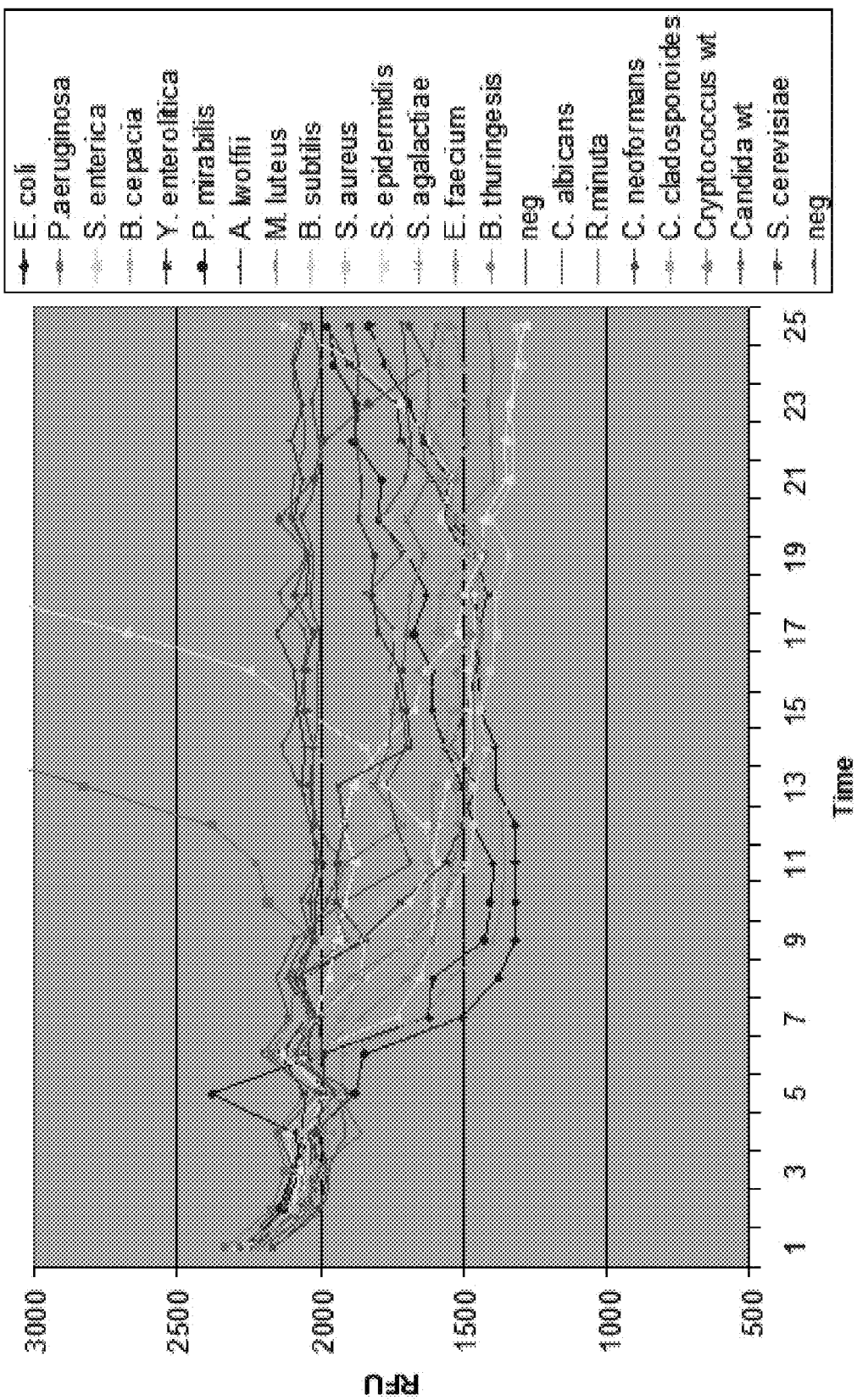

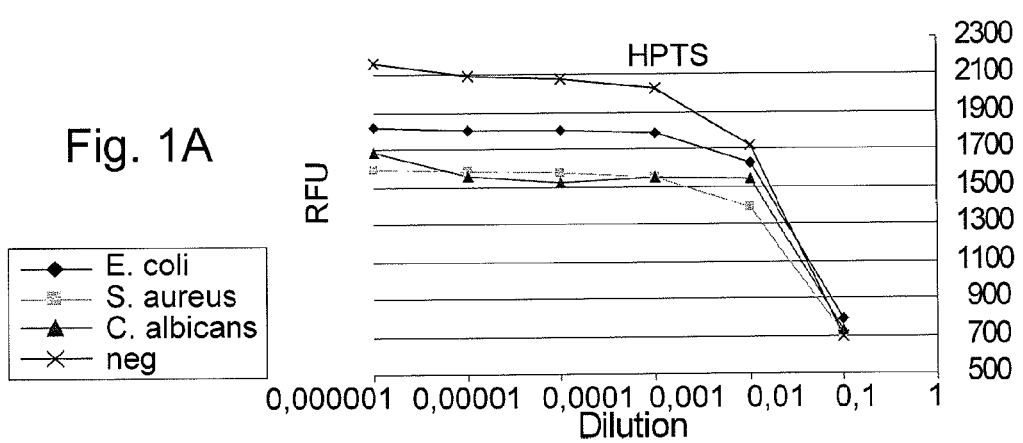
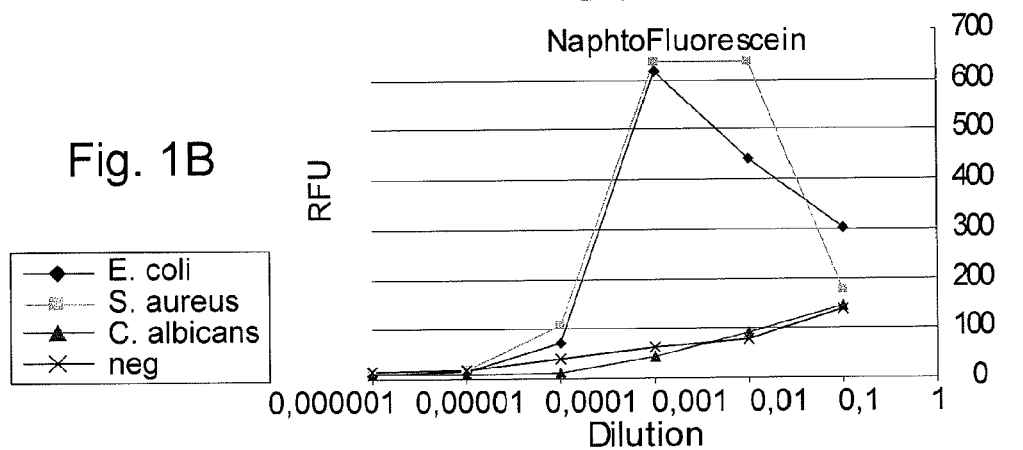
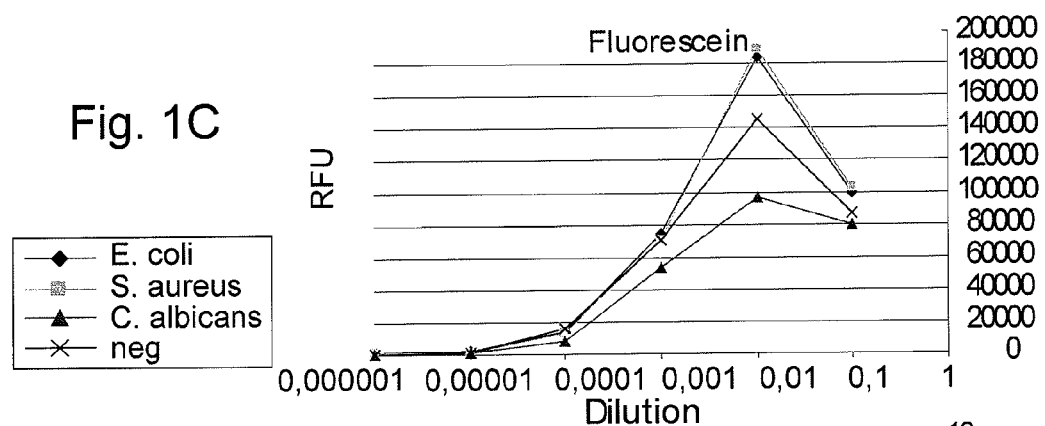
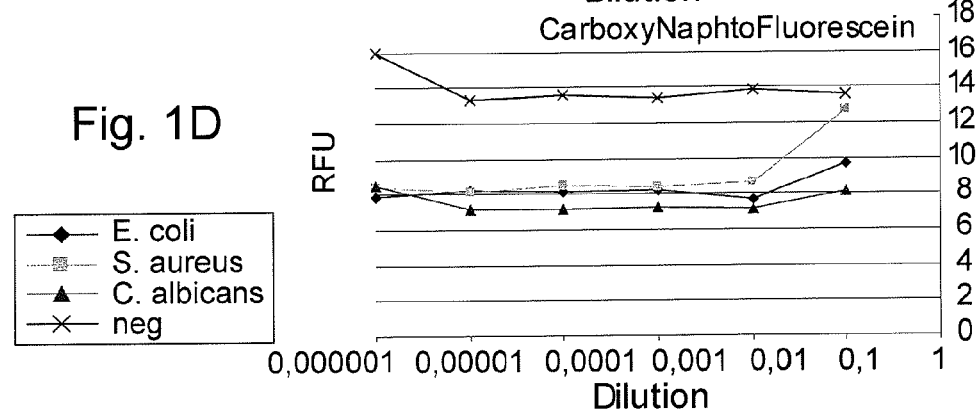

GROWTH MEDIUM FOR THE DETECTION OF MICROORGANISMS BY FLUORESCENCE ALLYING A FLUOROGENIC SUBSTRATE AND A PH-SENSITIVE FLUOROPHORE

The present application relates to a method and means for testing the sterility of aqueous or gaseous fluids used, in particular, in the manufacture of pharmaceutical products and devices.

In particular, it relates to a growth medium combining a fluorogenic substrate and a pH-sensitive fluorophor (in particular the combination of 4-methylumbeliferone (4-MU) and of fluorescein derivatives) which is of use for the detection of microorganisms by fluorescence, in particular by coupling the fluorescence measurements relating to the pH-sensitive fluorophor and the fluorescence measurements relating to the activation of the fluorogenic substrate(s) by the microorganisms.

The pharmaceutical industry is one of those sectors where the sterility constraints are very great, imposing constant monitoring of the quality of the products and of all the activities surrounding these products.

In terms of contamination by microorganisms, the testing is carried out using microbiological methods according to the regulations and standards stipulated in the pharmacopoeias.

The European or US pharmacopoeia defines several levels of microbiological quality of pharmaceutical preparations.

Products which are required to be sterile, such as parenteral preparations (injectable products, preparations for perfusions, etc.) and ophthalmic products, are characterized by a total absence of microorganisms capable of reproducing either by themselves or in a host organism.

Products which are not required to be sterile may contain a certain number of microorganisms, provided that the microbial contamination is contained below a certain threshold defined according to the criteria of the pharmacopoeia. The presence of these microorganisms does not represent any danger to the patient since this involves, for example, orally or rectally administered medicaments. The microbial flora and the acidic pH of the stomach prevent the development of the microorganisms, provided, however, that the number thereof does not exceed the criteria recommended by said pharmacopoeia. Various categories of non-sterile products are defined in the pharmacopoeia, each having their own requirements in terms of microbiological testing according to their end purpose.

The products to be tested are, moreover, in various solid or liquid forms and also in a variety of volumes and packaging. In this regard, a distinction can be made between filterable products, the microbiological testing of which can be carried out by means of filtration through a membrane, and non-filterable products, for which the pharmacopoeia recommends the technique of direct inoculation of the objected tested into a growth medium.

Preparations that can be tested by direct inoculation of the growth medium are generally solid, but can also have a fluid consistency, for instance oily liquids, to which a medium supplemented with 10 g/l of polysorbate 80 is added, and ointments and creams, to which suitable diluents or emulsifiers are added. It is customary for the volume of the object not to exceed 10% of the volume of the growth medium.

Depending on the regulatory requirements, various types of testing of microbiological quality can be carried out, ranging from the strict sterility test to specific counting of the main aerobic and anaerobic microorganisms, and including the targeted detection of specific microorganisms.

In general, when it is desired to have quite a precise idea of the type of microorganisms encountered, microbiologists prefer cultures on agar growth medium which make it possible to make a visual finding of the presence of the microorganisms, which form microcolonies within or on the agar. This approach makes it possible, if required, to sample the microorganisms forming these colonies, and to perform additional analyses for verification. Thus, when the microorganisms are different in nature, it is possible to determine, to a certain extent, the relative proportion of the various types of microorganisms encountered.

That being said, cultures on agar growth medium require time and manpower. Thus, the dividing time of slowly growing microorganisms, for instance *Methylobacter* sp. on a growth medium, such as R2A medium, intended to cause the growth of microorganisms stressed by a chlorine treatment, may be from 48 to 72 h [(Gallego V., Garcia M. T. and Ventosa A. (2006), *Methylobacterium adhaesivum* sp. nov., a methylotrophic bacterium isolated from drinking water. *Int. J. Syst. Evol Microbiol* 56, 339-342)]. Studies show, moreover, that a minimum incubation period of 14 days is necessary in order to really validate the absence of microorganisms in a sample [Bathgate, H. et al. (1993) *Journal of Parenteral Science and Technology* 47(5): 254-257].

In the context of inspection tests carried out in an industrial production chain, this period is too long to be able to rapidly deal with a contamination. This is because, if the contamination is established several days after the manufacture of a product, the recalling of this product for verification can cause high financial losses. The problem can also be one of public health, regarding the testing of the quality of drinking water, which is rapidly distributed after treatment.

Cultures in liquid medium, for their part, make it possible, to a certain extent, to reduce the manpower and the time for culturing the microorganisms. However, the risks of false positives linked to the handling of filter membranes and/or of the agar dishes are higher.

Transparent sterile preparation units, for instance those developed by the applicant (Steritest EZ, Millipore Corporation, Billerica, Mass. 01821, USA), for carrying out a sterility test after filtration of a liquid or gaseous sample have existed for several years. The principle is to retain, at the surface of the membrane, the possible contaminants contained in the sample that is filtered, and then, once the filtration of the sample has been carried out, to incubate the filter membrane inside the filter unit filled with sterile growth medium.

In the event of one or more contaminants being present, the medium, which is transparent, becomes cloudy owing to the development of the cells. The presence of microorganisms in the filter unit is then established visually.

Detection in liquid medium generally requires slightly more time than on agar growth medium, since a sufficient concentration of cells in the growth medium needs to be reached in order for the latter to become cloudy. Cultures in liquid medium are, however, generally more favorable to the growth of aerobic or anaerobic microorganisms.

Tests in liquid media have, on the other hand, certain limitations, among which is, in particular, the fact that it is impossible to estimate the number, the nature and the proportion of the contaminants initially present in the sample tested.

In this regard, tests carried out in a liquid growth medium only make it possible to provide a message of warning, but without providing information as to the nature of the microorganisms involved.

For these various reasons, it would be desirable to be able to have available tests in liquid medium that are faster and capable of giving a first indication as to the nature of the microorganisms identified.

At the very least, information on the types of microorganisms encountered (one or more species, aerobic or anaerobic, slow-growing or fast-growing, gram + or gram −, etc.), obtained at an early stage, would be advantageous so that a technician could be aware of the extent of the contamination and determine its origin.

In order to detect contaminations more rapidly, some methods use fluorogenic substrates which are incorporated into the growth media.

Fluorogenic substrates are complex molecules which, on contact with enzymes synthesized by microorganisms, are cleaved and become fluorescent. The fluorescence emitted is readily detectable with a spectrophotometer by illuminating the growth medium using radiation in the UV or visible spectrum, before the density of the cells is sufficient to make the growth medium cloudy. They therefore allow faster detection of contaminations.

Several families of fluorogenic substrates exist.

Nevertheless, these families of substrates have drawbacks which are particular to them and which limit their use in the context of sterility tests.

Fluorescein derivatives (CFA, CFDA) are, for example, fluorogenic substrates that are activated by a wide range of microorganisms; CFDA is thus commonly acknowledged to be a viability marker for prokaryotic or eukaryotic cells. These substrates are sensitive to the esterase activity of enzymes present in most microorganisms. However, this esterase activity is residually expressed in many growth media stipulated by the pharmacopeia, in particular those comprising yeast extracts or protein extracts. As a result, these substrates often undergo non-negligible abiotic hydrolysis [Clarke, J. M. et al., 2001, *Journal of microbiological methods*, 46: 261-267] and are, consequently, not very suitable for use in detection tests in liquid medium. Moreover, the strength of the fluorescence emitted by these substrates is sensitive to certain physical parameters of the growth medium, in particular the pH, which can have an influence on the reliability of the detection.

Methylumbelliferone derivatives (methylumbelliferyl), with the exception of some of their acetate or butyrate derivatives, are substrates that are much less sensitive to abiotic hydrolysis than fluorescein derivatives, but have a much narrower spectrum. However, there is a relatively wide choice of different substrates [Manafi, M., Kneifel, W. and Bascomb, S. (1991) Fluorogenic and chromogenic substrates used in bacterial diagnostics. *Microbiol Mol Biol Rev.* 55(3): 335-348] suitable for the specific detection of a certain number of common bacterial strains.

Nevertheless, the fluorescent emission spectra of these various methylumbelliferyl substrates tend to superimpose on one another, which limits their concomitant use for the purpose of distinguishing between various types of microorganisms simultaneously present in the same growth medium.

Another family of fluorogenic substrates, developed more recently by the company Biosynth, are the Aldols™.

These substrates have characteristics similar to those of the methylumbelliferone derivatives.

In particular, the aldols have a fluorescence emission spectrum very close to that of methylumbelliferyl compounds. Consequently, they also do not make it possible to distinguish between the microorganisms present in the same growth medium, nor to determine the relative proportion thereof.

With the aim of improving the specificity and the rapidity of sterility tests carried out in liquid medium, the present inventors had the idea of taking advantage of the specificities of the various families of substrates mentioned above, and of combining them so as to achieve sterility tests which are both faster and make it possible to obtain information on the type of microorganism detected.

To that end, the inventors have selected and simultaneously used Aldol or methylumbelliferyl fluorogenic substrates, which are stable in the usual growth media, and have combined them with substrates of which the fluorescence is, on the contrary, sensitive to variations in the pH of the growth medium, such as the fluorescein derivatives or HPTS.

Surprisingly, the inventors have noted that the measurements of fluorescence emitted, on the one hand, by the fluorogenic substrates (methylumbelliferyl or aldol derivatives) and, on the other hand, by the pH-sensitive fluorophors (fluorescein or HPTS), make it possible to detect a contamination early and to evaluate, to a certain extent, the type of microorganisms involved in the contamination.

In its general principle, the invention therefore comprises the simultaneous use of pH-sensitive and pH-insensitive fluorophors, with the aim of obtaining early universal detection of microorganisms, the coupling of the fluorescence measurements obtained, respectively, for the pH-sensitive fluorophor and the fluorophor activated by the live cells making it possible to obtain a signature characteristic of the microorganisms encountered.

FIG. 1: Experimental results preliminary to the invention. The various graphs represent the results of fluorescence measurements relating to the various pH-sensitive fluorophors, carried out during cultures of *E. coli, S. aureus* and *C. albicans* carried out for 24 hours using various concentrations for each molecule. 1A: HPTS. 1B: Naphthofluorescein. 1C: Fluorescein. 1D: Carboxynaphthofluorescein.

FIG. 2: Experimental results preliminary to the invention. The graph reports the fluorescence emitted by HPTS in the presence of various microorganisms during 24-hour cultures.

Figure 3:
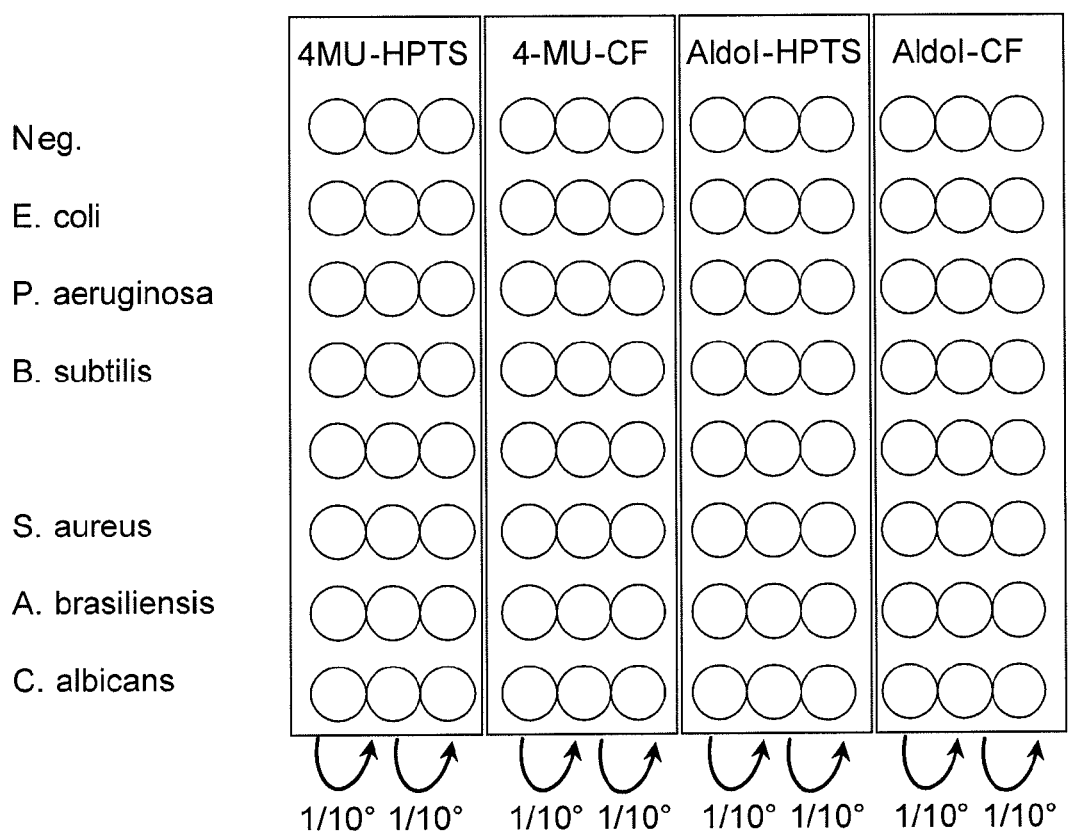

FIG. 3: Table recapitulating the various culture assays carried out according to the invention to obtain the experimental data represented in the graphs of FIGS. 4 to 7.

FIGS. 4 to 7: The graphs of FIGS. 4 to 7 represent the results of the measurements of fluorescence over time, relating to the various combinations of fluorescent compounds used, namely, respectively:
  4—4MU–HPTS combination;
  5—4MI–CF combination;
  6—Aldol–HPTS combination;
  7—Aldol–CF combination.

The measurements reported on these graphs are such that:
  Lm1 corresponds to the fluorescence emitted by the Aldols
  Lm2 corresponds to the fluorescence emitted by the HPTS
  Lm3 corresponds to the fluorescence emitted by the 4-MU
  Lm4 corresponds to the fluorescence emitted by the carboxyfluorescein (CF).

Each graph A to F corresponds to the culturing of a microorganism as indicated below:
  A—*E. coli*
  B—*P. aeruginosa*
  C—*B. subtilis*
  D—*S. aureus*
  E—*A. brasiliensis*
  F—*C. albicans*.

Graph G corresponds to the control measurements (uncontaminated growth medium comprising the above mentioned combinations).

FIG. 4: Comparison of the growth of the various microorganisms in the presence of the mixture of methylumbelliferyl derivatives (4-MU phosphate, 4-MU beta-glucopyranoside, 4-MU alpha-glucopyranoside, 4-MU beta-galactopyranoside) and of 8-hydroxypyrene-1,3,6-trisulfonic acid.

(4-MU–HPTS combination).

FIG. 5: Comparison of the growth of the various microorganisms in the presence of the mixture of methylumbelliferyl derivatives (4-MU phosphate, 4-MU beta-glucopyranoside, 4-MU alpha-glucopyranoside, 4-MU beta-galactopyranoside) and of 5,6-carboxyfluorescein.

(4MU–CF combination)

FIG. 6: Comparison of the growth of the various microorganisms in the presence of the mixture of the Aldol derivatives (Aldol 470 phosphate, Aldol 470 acetate, Aldol 455 beta-glucopyranoside, Aldol 455 beta-galactopyranoside) and of 8-hydroxypyrene-1,3,6-trisulfonic acid (HPTS).

(Aldol–HPTS combination)

FIG. 7: Comparison of the growth of the various microorganisms in the presence of the mixture of the Aldol derivatives (Aldol 470 phosphate, Aldol 470 acetate, Aldol 455 beta-glucopyranoside, Aldol 455 beta-galactopranoside) and of 5,6-carboxyfluorescein.

(Aldol–CF combination)

The present invention therefore comprises a method for detecting microorganisms which is of use, in particular, for carrying out a sterility test in liquid growth medium, characterized in that it comprises culturing, in a suitable medium, a sample for which it is sought to determine whether it is contaminated with a living microorganism.

This method applies to any form of filterable or non-filterable sample, in particular via direct inoculation of said sample into a previously sterile growth medium.

In this regard, it is possible to filter a liquid sample, such as water, or a gas, such as air, using a membrane. This membrane is then inoculated into a liquid growth medium, as if it formed a solid sample.

According to the invention, the detection method comprises one or more of the following steps:
  (i) placing a sample as defined above in a growth medium comprising:
    at least one fluorogenic substrate or a combination of fluorogenic substrates that can be activated by at least one enzyme of a microorganism, and
    at least one fluorophor, of which the fluorescence is indicative of the pH of said growth medium,
    in conditions which allow the growth of the microorganisms that are sought;
  (ii) analyzing said growth medium with regard to fluorescence in order to determine the fluorescence linked to the activation of the fluorogenic substrate contained in the growth medium by said microorganism, and to determine the fluorescence, indicative of the pH of the growth medium, emitted by the fluorophore;
  (iii) analyzing the fluorescence measurements determined for the fluorophor of which the fluorescence is indicative of the pH, and as well as for the fluorogenic substrate, so as to determine the presence or the absence of the type or types of microorganism that are sought in the growth medium.

The term "fluorogenic substrate" denotes a molecule that comprises a fluorophor group capable of absorbing light energy and of releasing all or part of this energy in the form of a fluorescence emission spectrum, and that also comprises a "quencher" group which masks the fluorescence of said fluorophor group.

On contact with specific enzymes of the microorganisms, the fluorogenic substrate adopts a different form, enabling the fluorophor to emit fluorescence. This activation results, either in a change in conformation of the molecule forming the substrate, or in cleavage of said molecule forming fluorescent residues.

Various fluorogenic substrates can be envisaged according to the invention. Fluorogenic substrates that are preferred according to the invention result, after enzymatic activation, in 4-methylumbelliferone compounds, the fluorescence emission of which is around 460±10 nm for an excitation wavelength of approximately 360±10 nm. Such fluorogenic substrates that are preferred according to the invention are, for example, methylumbelliferyl (4-MU) derivatives, in particular one or more substrates chosen from the following:

4-Methylumbelliferyl acetate (CAS: 2747-05-9)

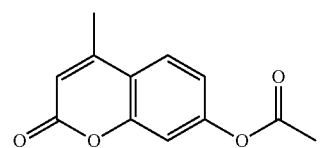 [SMILES: CC(=O)Oc1ccc2c(C)cc(=O)oc2c1]

4-Methylumbelliferyl caprylate (CAS: 2067-66-3)

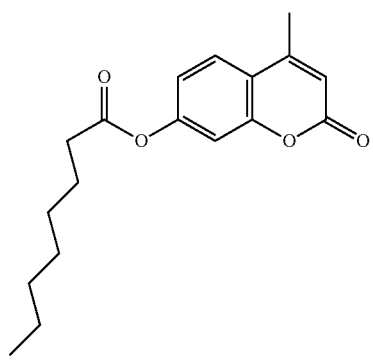 [SMILES: CCCCCCCC(=O)Oc1ccc2c(C)cc(=O)oc2c1]

4-Methylumbelliferyl α-D-glucopyranoside (CAS: 17833-43-1)

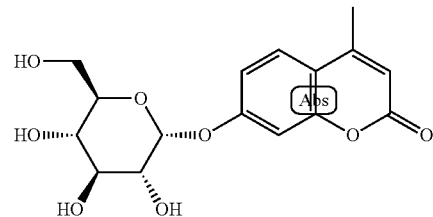 [SMILES: Cc1cc(=O)oc2cc(O[C@H]3O[C@H](CO)[C@@H](O)[C@H](O)[C@H]3O)ccc12]

4-Methylumbelliferyl β-D-glucopyranoside (CAS: 18997-57-4)

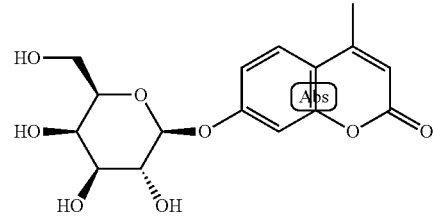 [SMILES: Cc1cc(=O)oc2cc(O[C@@H]3O[C@H](CO)[C@H](O)[C@H](O)[C@H]3O)ccc12]

4-Methylumbelliferyl α-D-galactopyranoside (CAS: 38597-12-5)

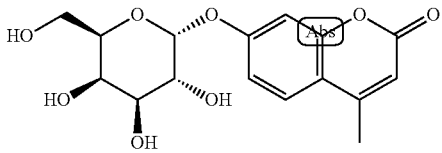 [SMILES: Cc1cc(=O)oc2cc(O[C@H]3O[C@H](CO)[C@H](O)[C@H](O)[C@H]3O)ccc12]

4-Methylumbelliferyl β-D-galactopyranoside (CAS: 6160-78-7)

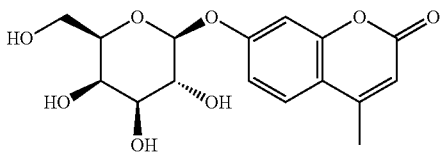 [SMILES: Cc1cc(=O)oc2cc(O[C@@H]3O[C@H](CO)[C@H](O)[C@H](O)[C@H]3O)ccc12]

4-Methylumbelliferyl phosphate (CAS: 3368-04-5)

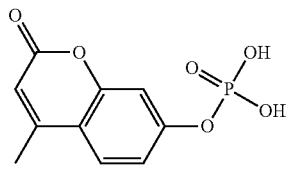 [SMILES: Cc1cc(=O)oc2cc(OP(=O)(O)O)ccc12]

Since these substrates are relatively specific for a category of microorganisms, i.e. activated only by certain enzymes which are not present in all microorganisms, it is advantageous, according to the invention, to select several thereof, so as to broaden the spectrum of detection.

The inventors have determined, more particularly, that the combination of four methylumbelliferyl derivatives selected from the above-mentioned compounds is advantageous, in particular the combination including 4-MU phosphate, 4-MU alpha-D-glucopyranoside (or alpha-D-glucoside), 4-MU beta-D-glucopyranoside (or beta-D-glucoside) and 4-MU beta-D-galapyranoctoside (or beta-D-galactoside). This combination makes it possible to detect most of the microorganisms commonly sought, in particular the following: gram-negative bacteria such as E. coli and P. aeruginosa, gram-positive bacteria, B. subtilis and S. aureus, and the fungi C. albicans and A. brasiliensis.

The invention is not, however, limited to only these species, and the term "microorganism" should be understood to denote any living cell capable of multiplying autonomously. The term "cell" is intended to mean a cytoplasm delimited by a membrane, comprising genes.

The compounds sold under the name Aldol™ (Biosynth AG, Rietlisstrasse 4, 9422 Staad, Switzerland) are preferred substrates according to the invention, in the same way as the previous ones, in particular the compounds Aldol 470 (1-[2-(2,4-dimethoxybenzoyl)phenyl]-1H-indol-3-yl) and Aldol 455 (1-(2-benzoylphenyl)-6-chloro-1H-indol-3-yl), and also the derivatives thereof, in particular the acetate, phosphate, beta-galactoside and beta-glucoside derivatives of said compounds. These compounds are described in the European Patent Application filed under No. 09159639. These compounds have the advantage of being activatable in aerobic conditions, just as they are in anaerobic conditions, without producing any toxicity with respect to the microorganisms.

For the purpose of the present invention, "a fluorophor of which the fluorescence is indicative of the pH of said growth medium" denotes a molecule of which the strength of fluorescence emission varies according to the change in pH in the growth medium, or of which the emission wavelength varies according to this same change in pH for a constant excitation wavelength, the concentration of said molecule in the medium remaining substantially constant. Preferably, said variations in fluorescence are observed in a pH range of between 3 and 10, preferably between 5 and 9, more preferentially between 6 and 8. The molecular mechanisms that explain these variations in fluorescence as a function of pH have been described, for example, for certain cyanine derivatives [Briggs M. S. et al. (2000) Chem. Commun. 2323-2324].

The term "variation in fluorescence" is intended to mean a variation in the RFU (relative fluorescence unit) of at least 10%, preferably of at least 20%, and more preferentially of at least 30%, for a variation of one pH unit.

The fluorophors of which the fluorescence is indicative of the pH of said growth medium, preferred according to the invention, are selected from 8-hydroxypyrene-1,3,6-trisulfonic acid or a salt thereof, the cyanine compounds or a derivative thereof, in particular pentamethine cyanine or a compound comprising fluorescein or a derivative, salt or ester thereof.

Among the compounds comprising fluorescein, carboxyfluorescein is preferred, in particular 5(6)-carboxyfluorescein (CAS 72088-94-9).

A preferred fluorophor of the invention is also 8-hydroxypyrene-1,3,6-trisulfonic acid trisodium salt (HPTS) (CAS 27928-00-3).

The combination of CF and 4-MU is preferred according to the invention. Specifically, the coupling of the fluorescence measurements carried out in relation to one or other of the fluorescence emission spectra of these compounds has allowed early and specific detection of microorganisms.

Preferably, 4-MU compounds are not used as fluorescent molecules indicative of the pH, according to the invention, as they are generally unreliable pH indicators.

As emerges from the experimental examples presented later in the present application, the respective variations, over time, of the fluorescence linked to one or other of the fluorescent compounds are different for each type of microorganism, and this forms a unique signature for each of them, which can be detected at an early stage of the method for detecting microorganisms.

The combinations, according to the invention, of one or more Aldol compounds and of carboxyfluorescein, or of HPTS and of one or more methylumbelliferyl derivatives, are also found to be relevant for detecting and obtaining a microorganism-specific signature. The profiles obtained can be at least partly explained by differences in metabolism between the various species of microorganisms (influence on the pH of the medium, growth rate, strength of fluorescent substrate activation, etc.).

In one of its fundamental aspects, the invention concerns the coupling of the fluorescence measurements originating respectively from the activation of the fluorogenic substrate and of the pH-sensitive fluorophor, in the same growth medium, with the aim of identifying the type of microorganism present in this growth medium. The term "coupling" is intended to mean determining the relationship between the fluorescence measurement accounting for the activation of the fluorogenic substrate with the other fluorescence measurement accounting for the variation in pH of the growth medium. Preferably, this relationship is established according to a time variable (t), by calculation or in the form of a graphical representation. According to a preferred aspect of the invention, the coupling of these data makes it possible to obtain a description of the change in the growth medium particular to the various types of microorganisms, integrating the variables of pH, time and microbial enzyme activity.

Thus, the method for detecting microorganisms according to the invention can include, in step ii) described above, the fact that the fluorescence is measured at regular intervals to obtain a variation in fluorescence as a function of time. Preferably, the fluorescence is measured every 30 seconds, more preferably every minute, even more preferably every two minutes. Similarly, in step iii), the fluorescence measurements can be compared with standard measurements referenced in a database, making it possible to distinguish more clearly between the various types of microorganisms.

In one of its aspects, the invention concerns a growth medium for more particularly implementing the method according to the invention, which is made up of a liquid or solid nutritive support, in which at least one fluorogenic substrate or combination of these substrates, and at least one fluorophor of which the fluorescence is indicative of the pH of said growth medium, as defined above respectively, are uniformly solubilized.

The nutritive support is most commonly a conventional medium already described not including fluorescent agents.

The fluorescence particular to the nutritive support is, in addition, preferably insensitive to the variations in pH of the growth medium, and also to the introduction of said microorganisms into the growth medium. In other words, it should be preferentially taken care that the growth medium itself does not experience variations in fluorescence capable of interfering with the fluorescence emitted by the fluorophors.

The conditions for culturing the microorganisms are substantially the same as those described in the literature, in particular in the pharmacopeia, for a conventional medium.

Although initially designed for cultures in liquid medium, there is nothing to stop the invention being implemented with agar growth media using suitable devices for measuring fluorescence (for example a scanning cytometer), which are known to the person skilled in the art.

A growth medium according to the invention preferably comprises, as fluorogenic substrate(s) and fluorophor(s), the compounds or combinations of compounds detailed above.

According to a preferred aspect of the invention, the method for detecting microorganisms may comprise a step i) in which the microorganism(s) is (are) filtered beforehand onto a membrane before being placed in culture.

The invention is also directed toward a kit for detecting microorganisms, characterized in that it comprises a growth medium according to the invention, alternatively in the form of separate packaging with a view to being mixed:
  a conventional growth medium for microorganisms;
  at least one fluorogenic substrate or a combination of fluorogenic substrates soluble in said growth medium; and
  at least one fluorophor, soluble in said growth medium, of which the fluorescence is indicative of the pH of said growth medium.

The growth medium may be packaged in dehydrated form for the needs of storage or convenience.

Such a detection kit may furthermore comprise a membrane for carrying out a sterility test preceded by a filtration step. Such a filter membrane may be monolayer or multilayer. It is in general constituted of one or more materials chosen from polytetrafluoroethylene, polyvinylidene fluoride (PVDF), polycarbonate, polyamide, polyester, polyethersulfone, acetylcellulose and nitrocellulose. An example of this type of membrane is sold by the applicant under the reference HAWG Milliflex, Millipore.

A kit according to the invention may furthermore comprise a filter unit, bottle or bag, which are preferably sterile, intended to receive the growth medium for carrying out a sterility test.

The following examples are intended to supplement the description of the invention without introducing any limitation thereto.

EXAMPLE

1/ Preparation of the Growth Media 100 mL of liquid TSB (Biomerieux) medium was prepared and sterilized according to the recommendations of the manufacturer. Next, according to the various combinations defined below, the following solutions of pH-sensitive fluorophore and fluorogenic substrates were added in sterile conditions to the TSB medium.

pH-Sensitive Fluorophores:
HTPS:
  30 µL of a sterile stock solution at 10 mM of 8-hydroxypyrene-1,3,6-trisulfonic acid, or
CF:
  20 µL of a sterile stock solution at 100 µM of 5,6-carboxyfluorescein;
Fluorogenic Substrates:
Aldols:
  200 µL of the sterile mix of Aldol derivatives (Aldol 470 phosphate, Aldol 470 acetate, aldol 455 beta-D-glucopyranoside, aldol 455 beta-D-galactopyranoside) where the stock concentration of each derivative is 25 mg/mL; or
4-MU:
  200 µL of the sterile mix of 4-methylumbelliferyl derivatives (4-MU phosphate, 4-MU beta-D-glucopyranoside, 4-MU alpha-D-glucopyranoside, 4-MU beta-D-galactopyranoside) (4-MU) where the stock concentration of each derivative is 50 mg/mL.

The fluorophore solutions and fluorogenic substrates were sterilized beforehand using a Stericup filter unit having a filter membrane with 0.22 µm pores before being incorporated to form the growth media tested.

References of the products used (catalog reference #):
TSB: Biomerieux #41146
HPTS: Fluka #56360
5,6-carboxyfluorescein: Sigma #21877
Aldol 470 phosphate: Biosynth #A-4678
Aldol 470 acetate: Biosynth #A-4680
Aldol 455 beta-D-glucopyranoside: Biosynth #A-4689
Aldol 455 beta-D-galactopyranoside: Biosynth #A-4684
4-MU phosphate: Glycosynth #44093
4-MU beta-D-glucopyranoside: Glycosynth #44059
4-MU alpha-D-glucopyranoside: Glycosynth #44051
4-MU beta-D-galactopyranoside: Glycosynth #44045

2/ Preparation of the Suspensions of Microorganisms

The tests were carried out with the following microorganisms:
  A *E. coli* ATCC 8739
  B *P. aeruginosa* ATCC 9027
  C *B. subtilis* ATCC 6633
  D *S. aureus* ATCC 6538

E A. brasiliensis ATCC 16404
F C. albicans DSMZ 1386

Each microorganism strain was diluted to attain an initial concentration varying between $10^3$ and $10^4$ cells/mL ($10^2$ cells/mL for A. brasiliensis).

3/ Preparation of the Cultures on a Plate with 96 Wells

A Greiner Bio-One µClear Plate with 96 wells having reference 655090 was used for the assays.

The inocula for each strain were introduced into the first column of each growth medium series, then diluted to 1/10° in series.

FIG. 3 recapitulates the different culture assays carried out, which are conducted using the growth media indicated below.

For the 4MU–HPTS Combination:
TSB
Mixture of methylumbelliferyl derivatives (4-MU phosphate, 4-MU beta-glucopyranoside, 4-MU alpha-glucopyranoside, 4-MU beta-galactopyranoside) and
8-hydroxypyrene-1,3,6-trisulfonic acid.

For the 4MU–CF Combination:
TSB
Mixture of methylumbelliferyl derivatives (4-MU phosphate, 4-MU beta-glucopyranoside, 4-MU alpha-glucopyranoside, 4-MU beta-galactopyranoside) and
5,6-carboxyfluorescein (CF.).

For the Aldol–HPTS Combination:
TSB
Mixture of the Aldol derivatives (Aldol 470 phosphate, Aldol 470 acetate, aldol 455 beta-glucopyranoside, aldol 455 beta-galactopyranoside) and
8-hydroxypyrene-1,3,6-trisulfonic acid (HPTS).

For the Aldol–CF Combination:
TSB
Mixture of the Aldol derivatives (Aldol 470 phosphate, Aldol 470 acetate, aldol 455 beta-glucopyranoside, aldol 455 beta-galactopyranoside), and
5,6-carboxyfluorescein (CF).

Each of the above media is tested for each of the microorganisms with three different dilutions.

The 96-well plate reader of trademark Gemini was programmed so as to perform one acquisition every 30 minutes over 72 h, i.e. 145 points of measurement.

The acquisition for the fluorescence values was carried out by an optical reader from the bottom of the wells.

Each well is the subject of 10 measurements and the average value is recorded.

For each well, 4 types of measurement are carried out:
1—Lm1: Exc: 355 nm Em: 555 nm cutoff: 530 nm
2—Lm2: Exc: 403 nm Em: 451 nm cutoff: 435 nm
3—Lm3: Exc: 360 nm Em: 455 nm cutoff: 435 nm
4—Lm4: Exc: 485 nm Em: 525 nm cutoff: 595 nm The acquisition on the Lm1 channel enables the fluorescence of the aldols to be measured.

The acquisition on the Lm2 channel enables the fluorescence of the HPTS to be measured.

The acquisition on the Lm3 channel enables the fluorescence of the 4-MU to be measured.

The acquisition on the Lm4 channel enables the fluorescence of the CF to be measured.

The acquisition kinetics were produced using the softmax Pro software.

4/ Analysis of the Results Obtained

The results of the fluorescence measurements are shown in the form of graphs in FIGS. 4 to 7.

FIGS. 4A to 4G concern the 4-MU+HPTS combination.
FIGS. 5A to 5G concern the 4-MU+CF combination.
FIGS. 6A to 6G concern the Aldol+HPTS combination.
FIGS. 7A to 7G concern the Aldol+CF combination.

The graphs denoted G correspond to the uncontaminated negative control.

Figure 4A:
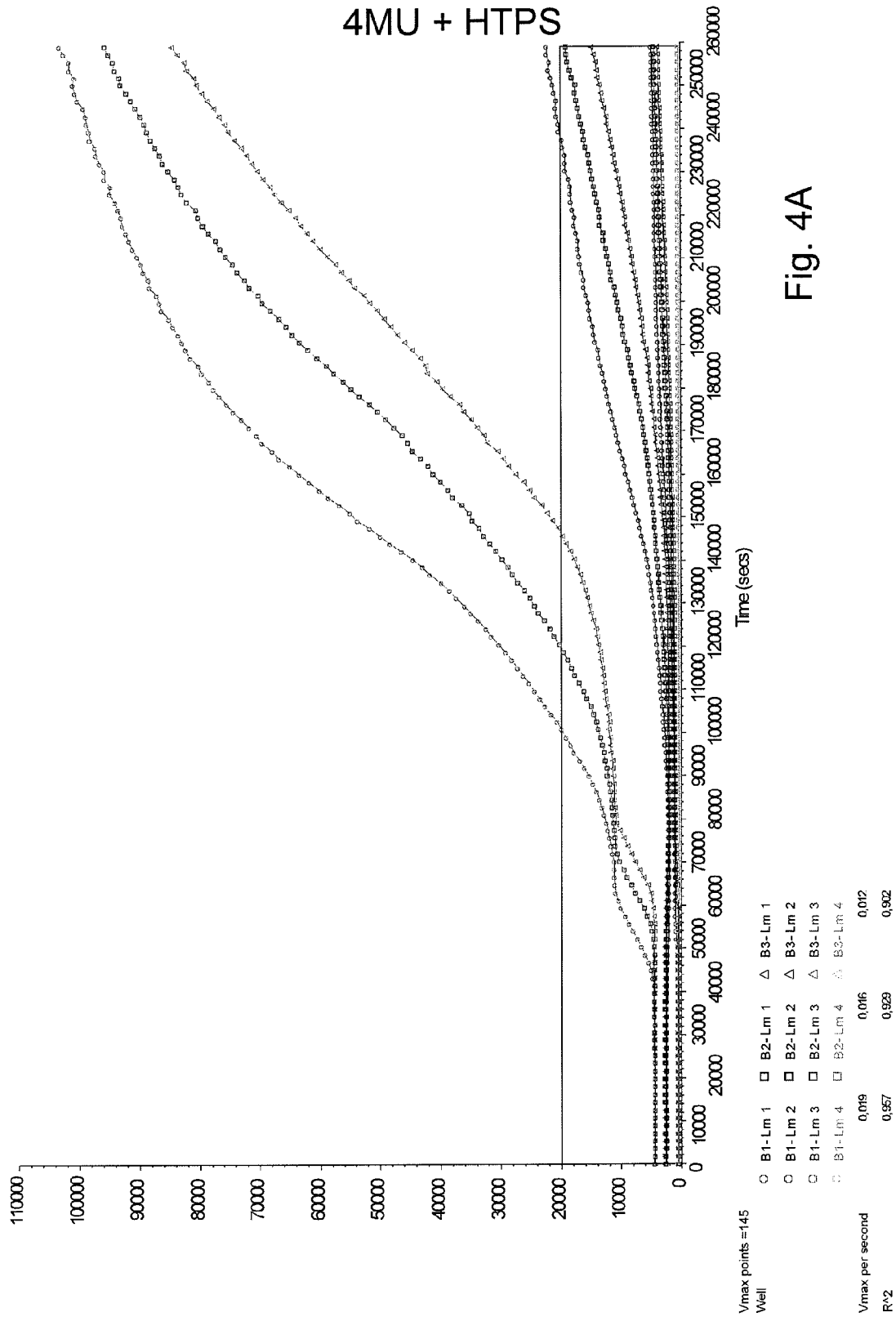
Figure 4B:
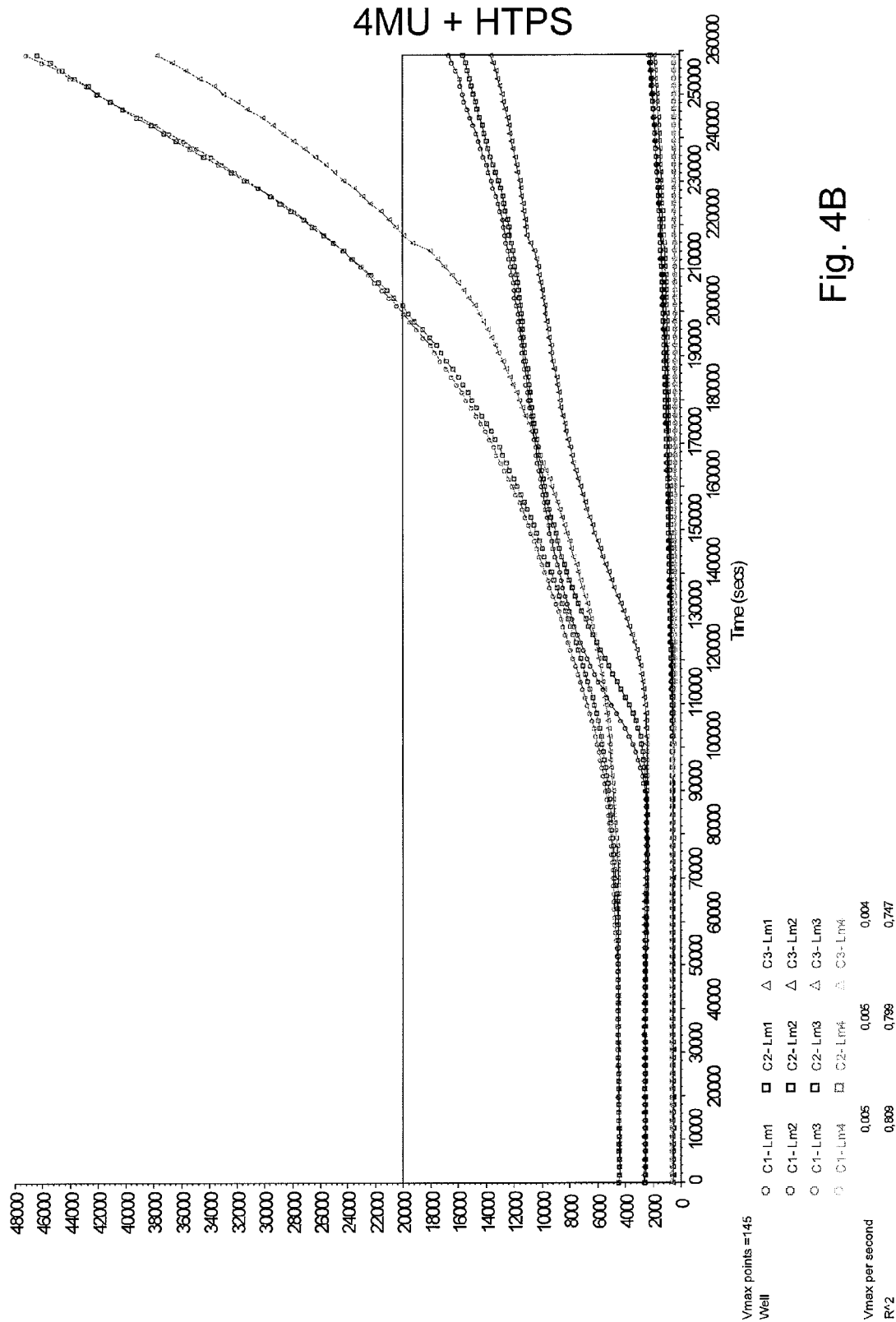
Figure 4C:
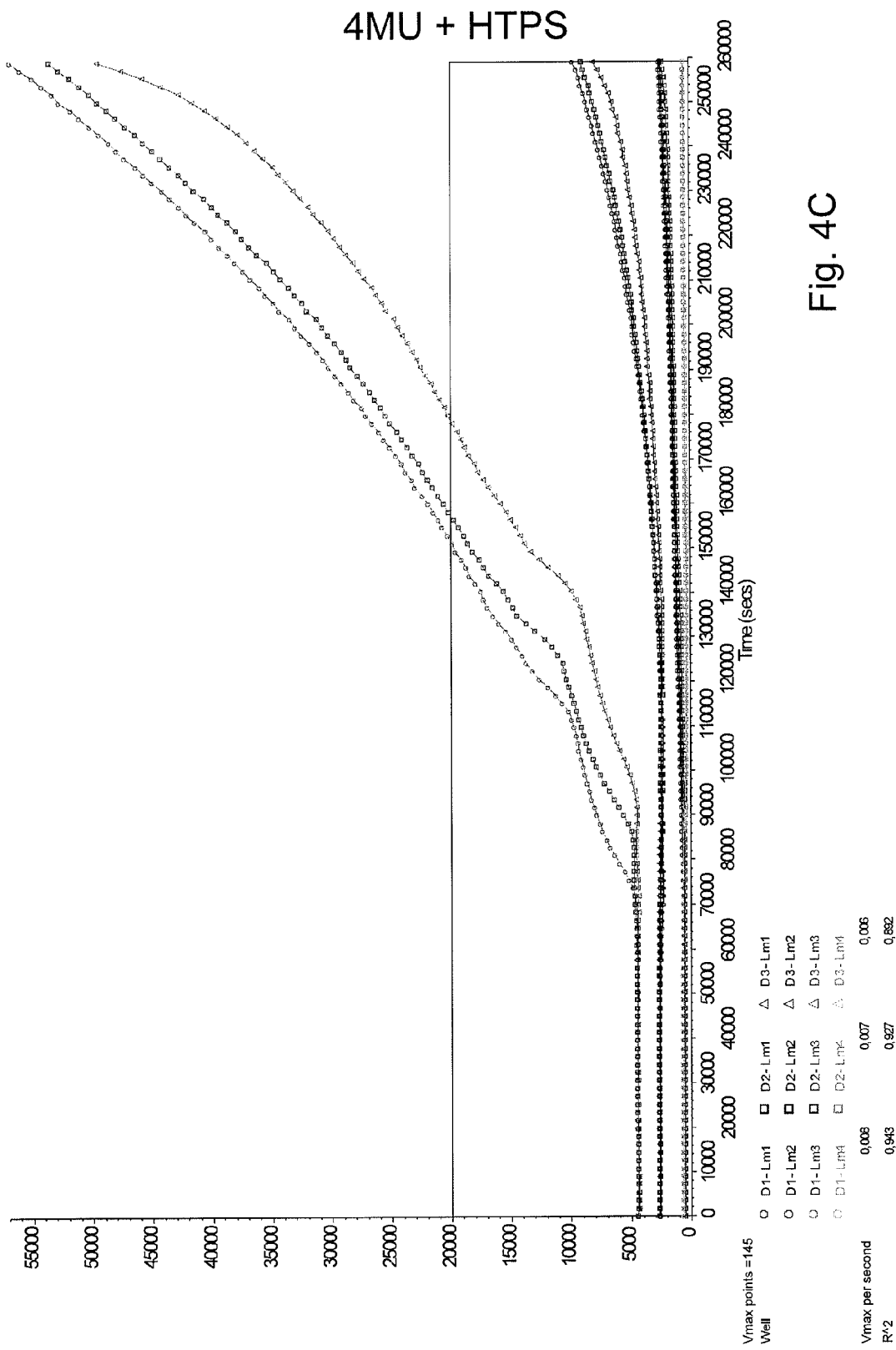
Figure 6A:
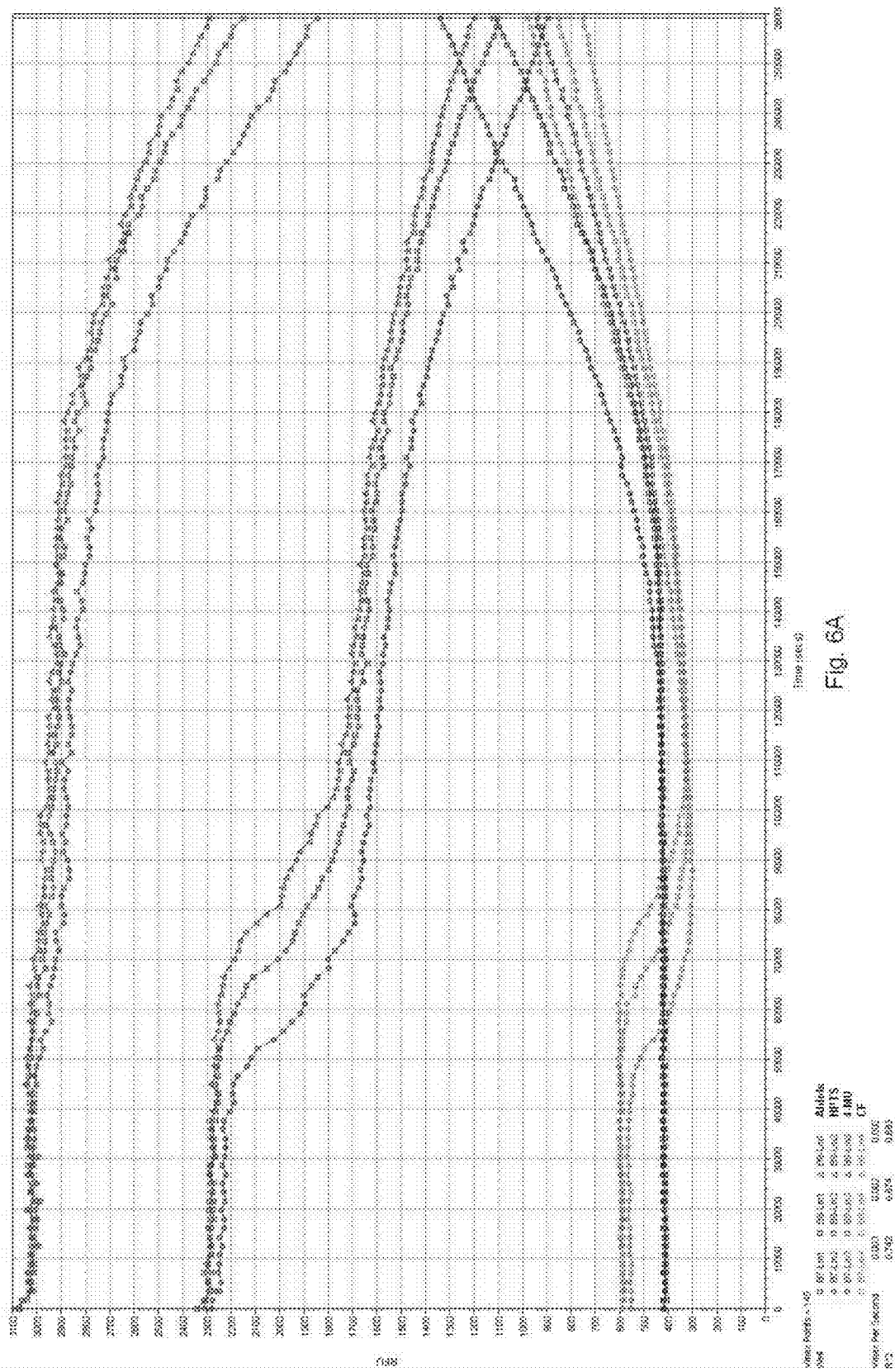
Figure 6B:
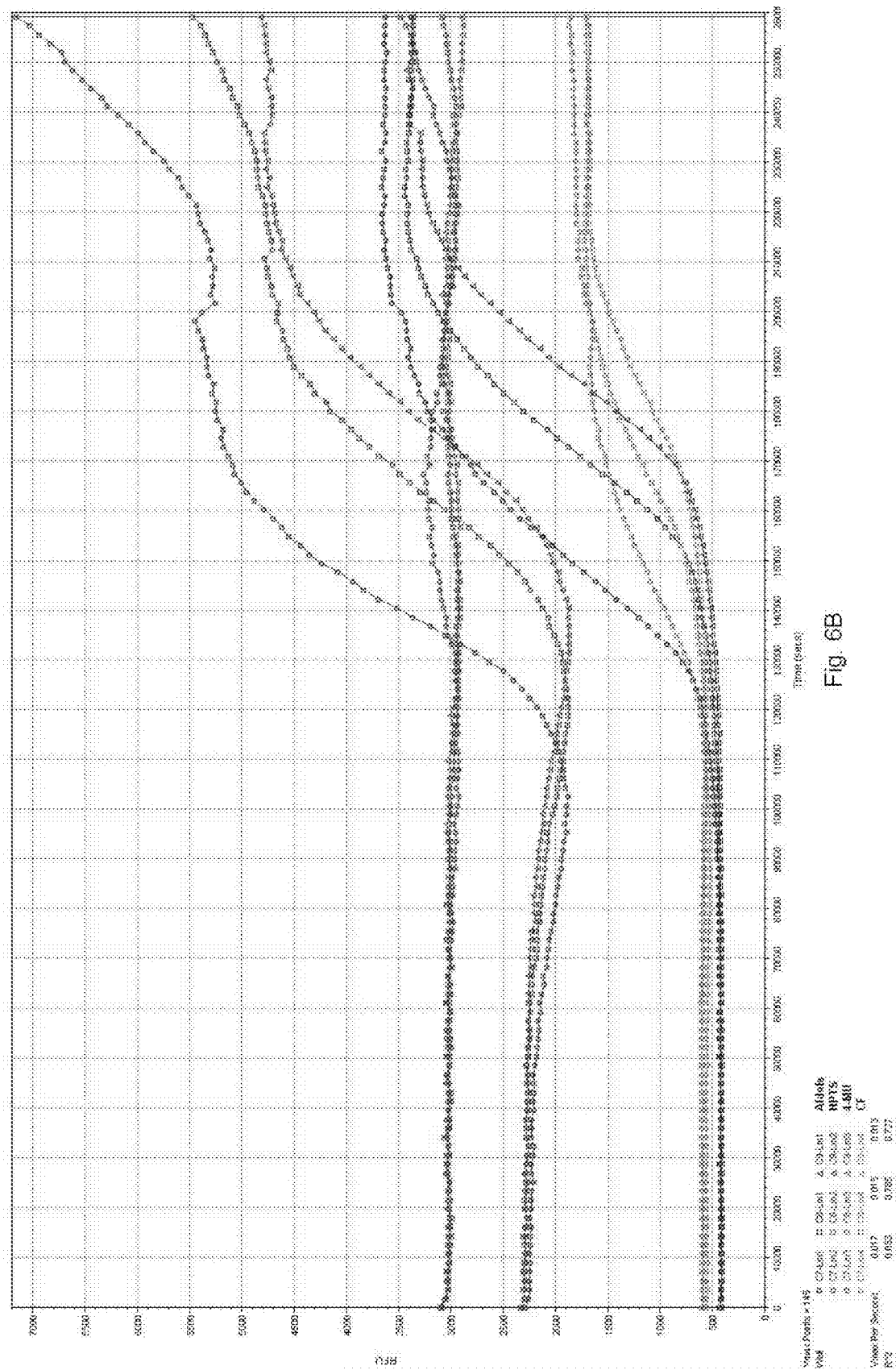
Figure 6C:
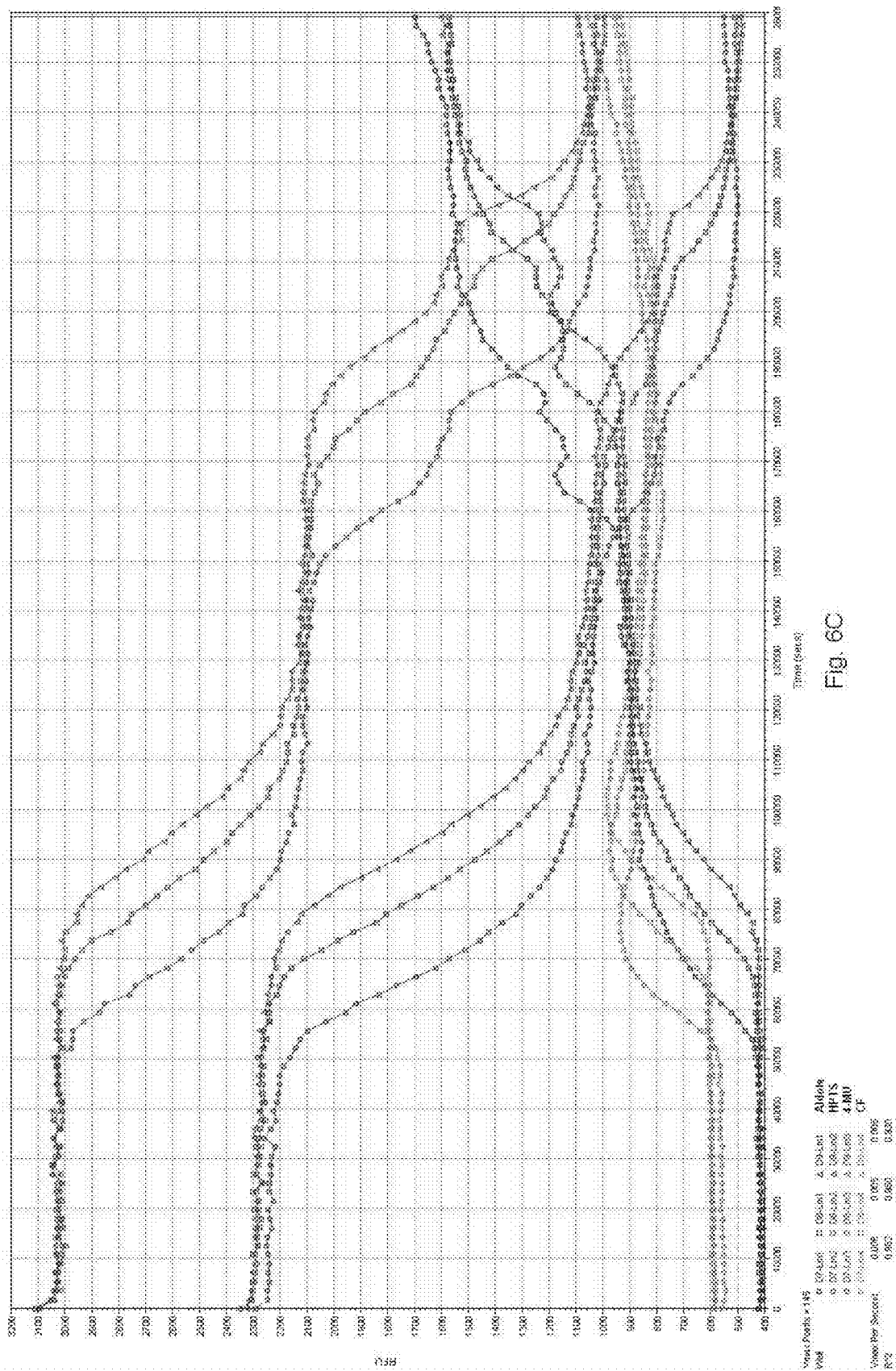
Figure 6D:
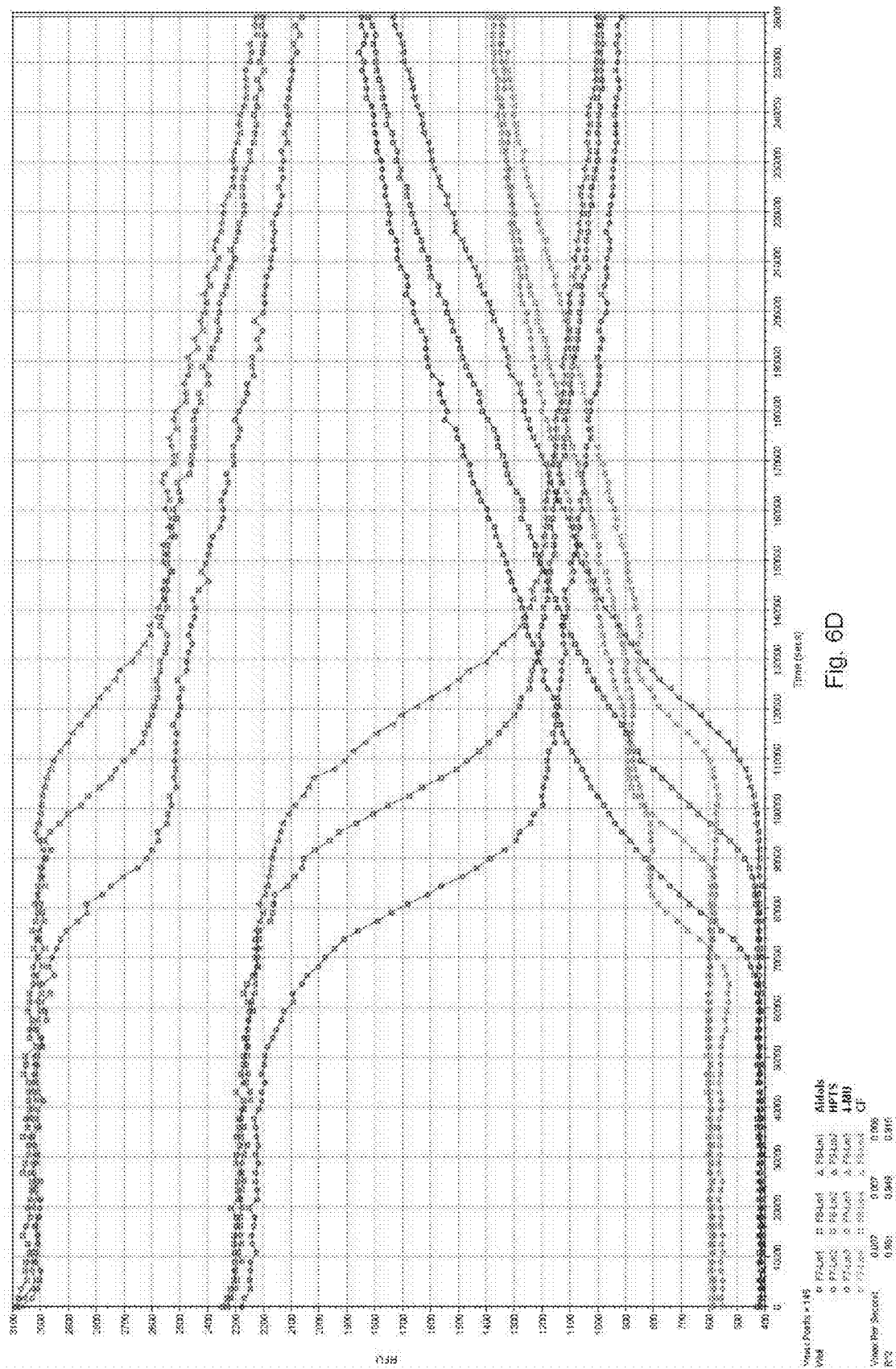
Figure 6E:
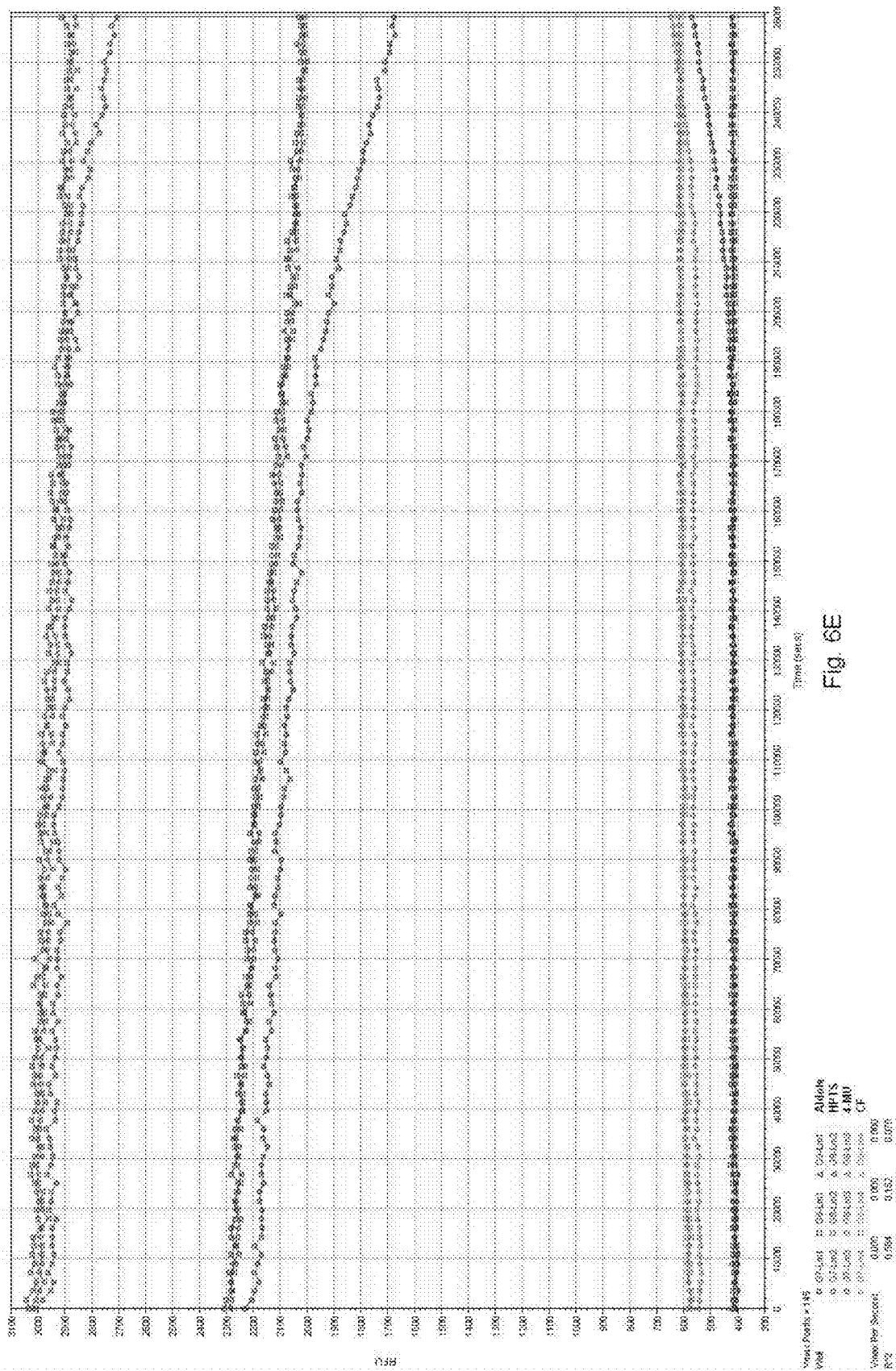
Figure 6F:
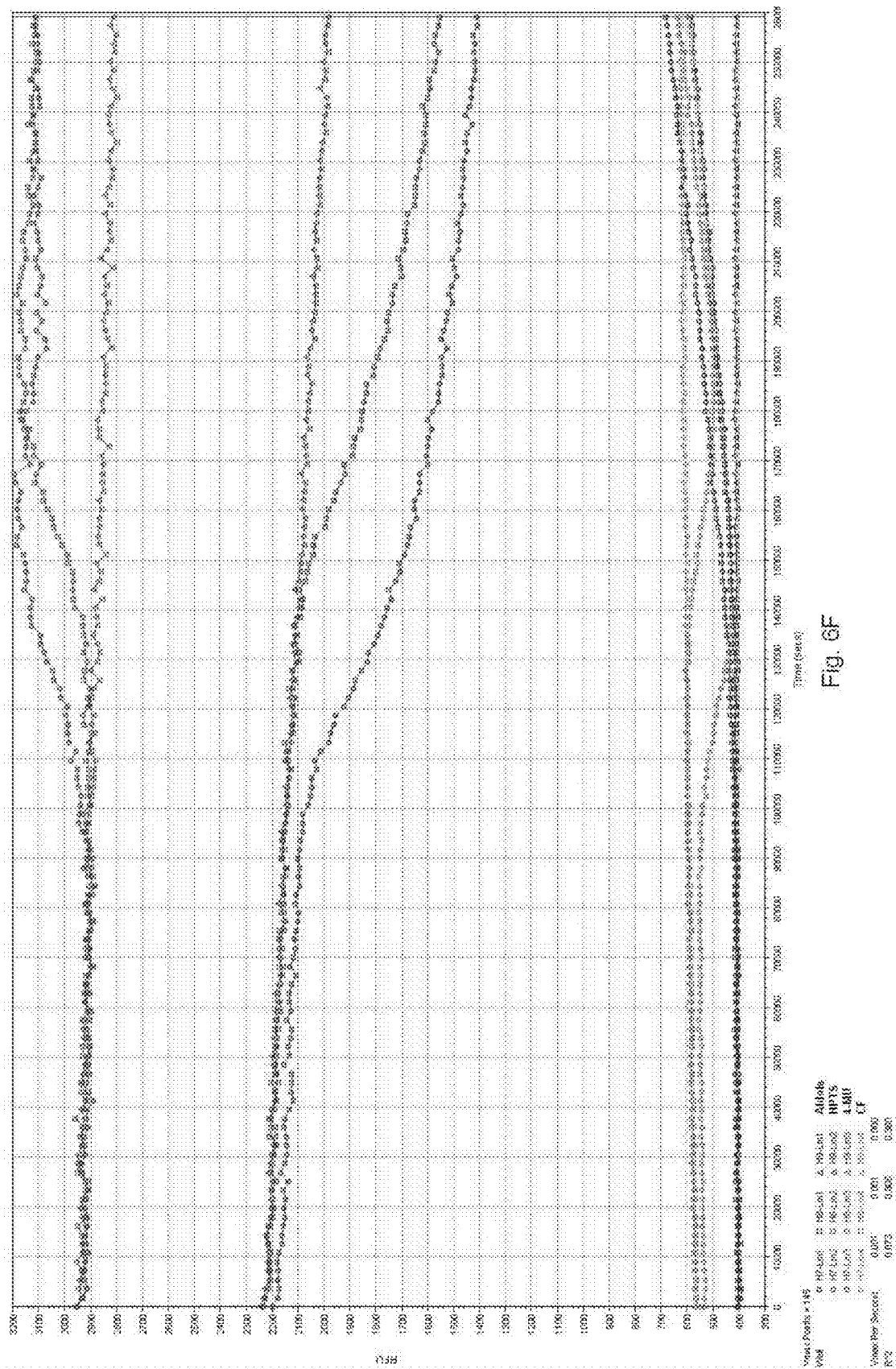
Figure 7A:
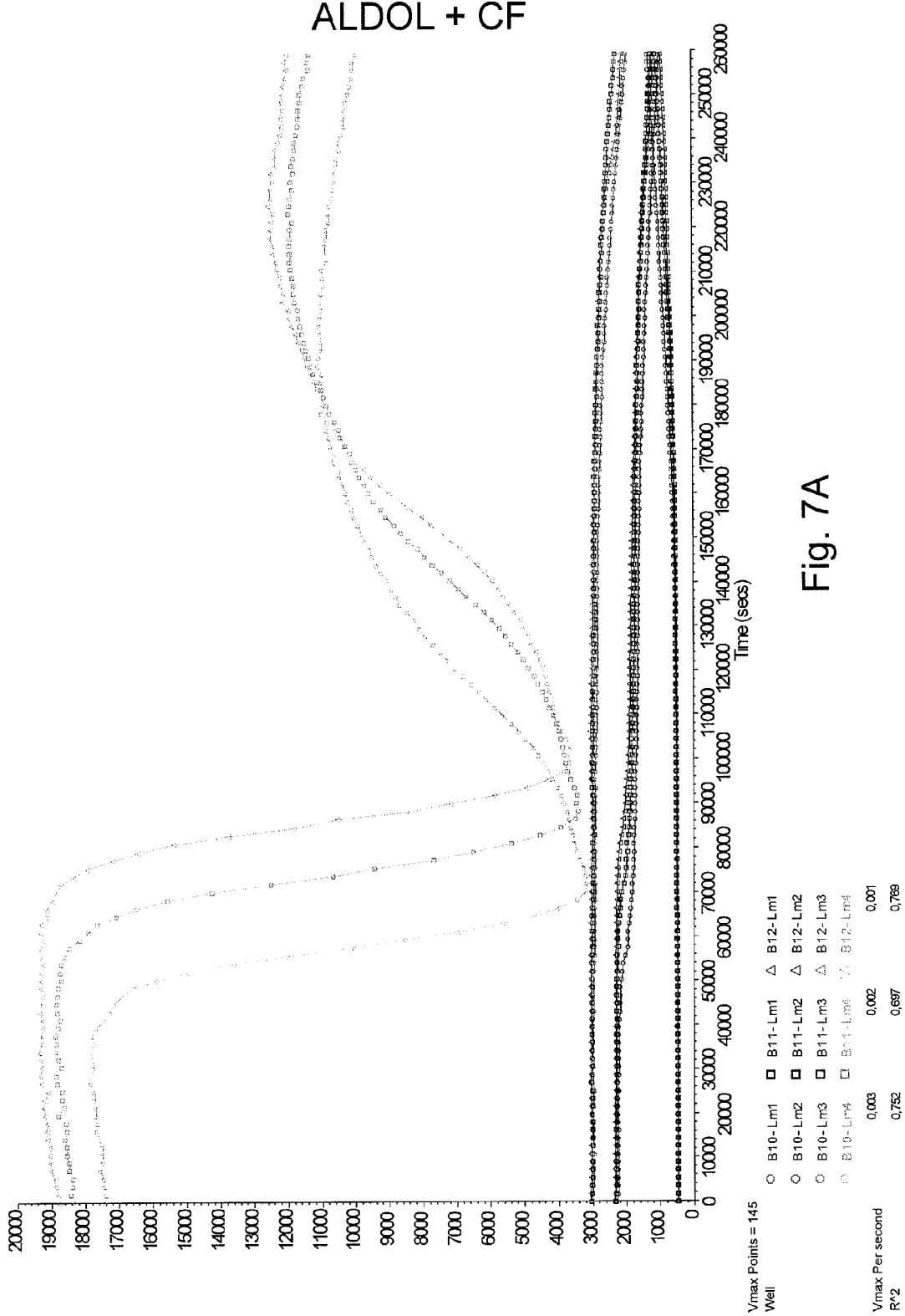
Figure 7B:
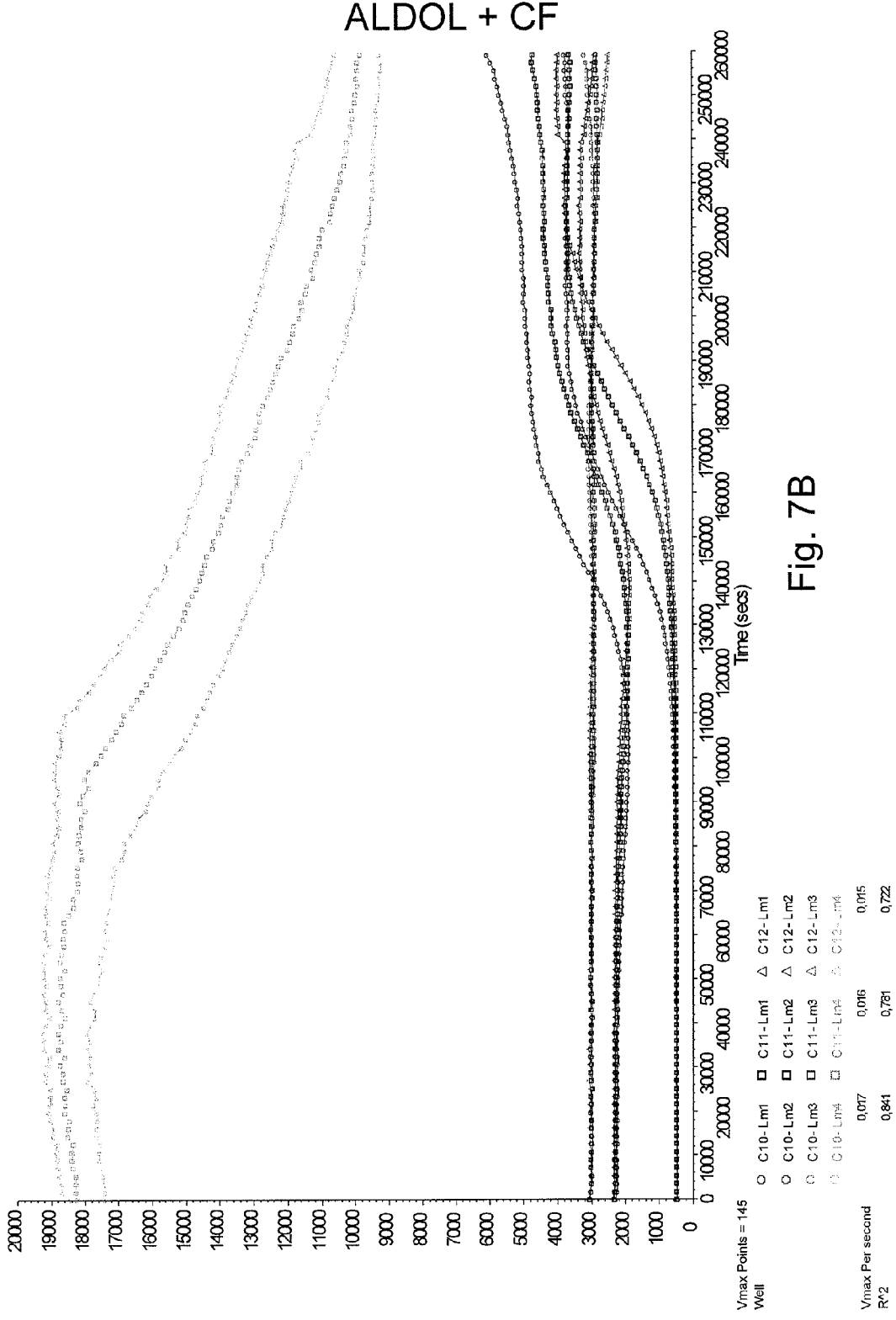
Figure 7C:
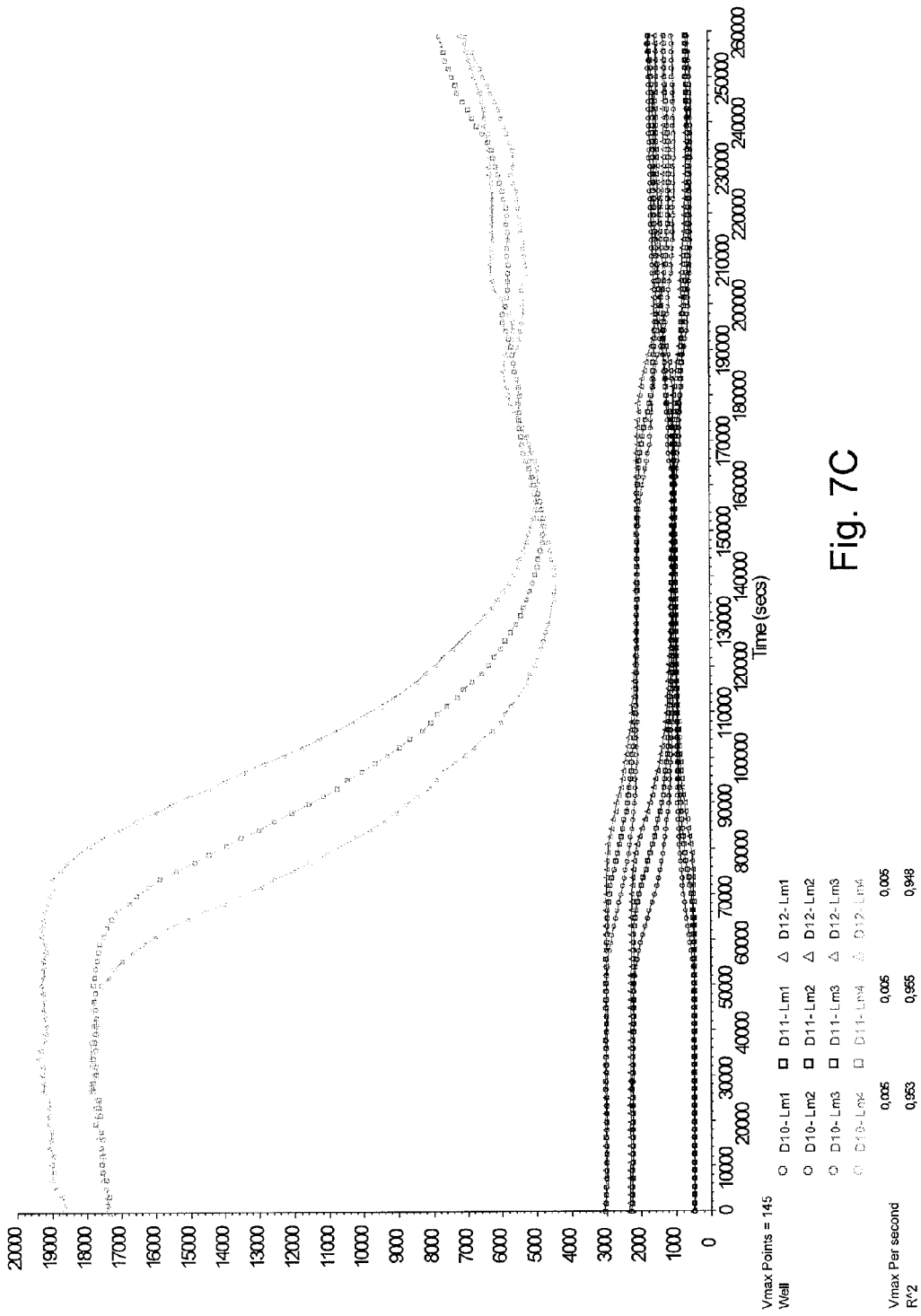
Figure 7D:
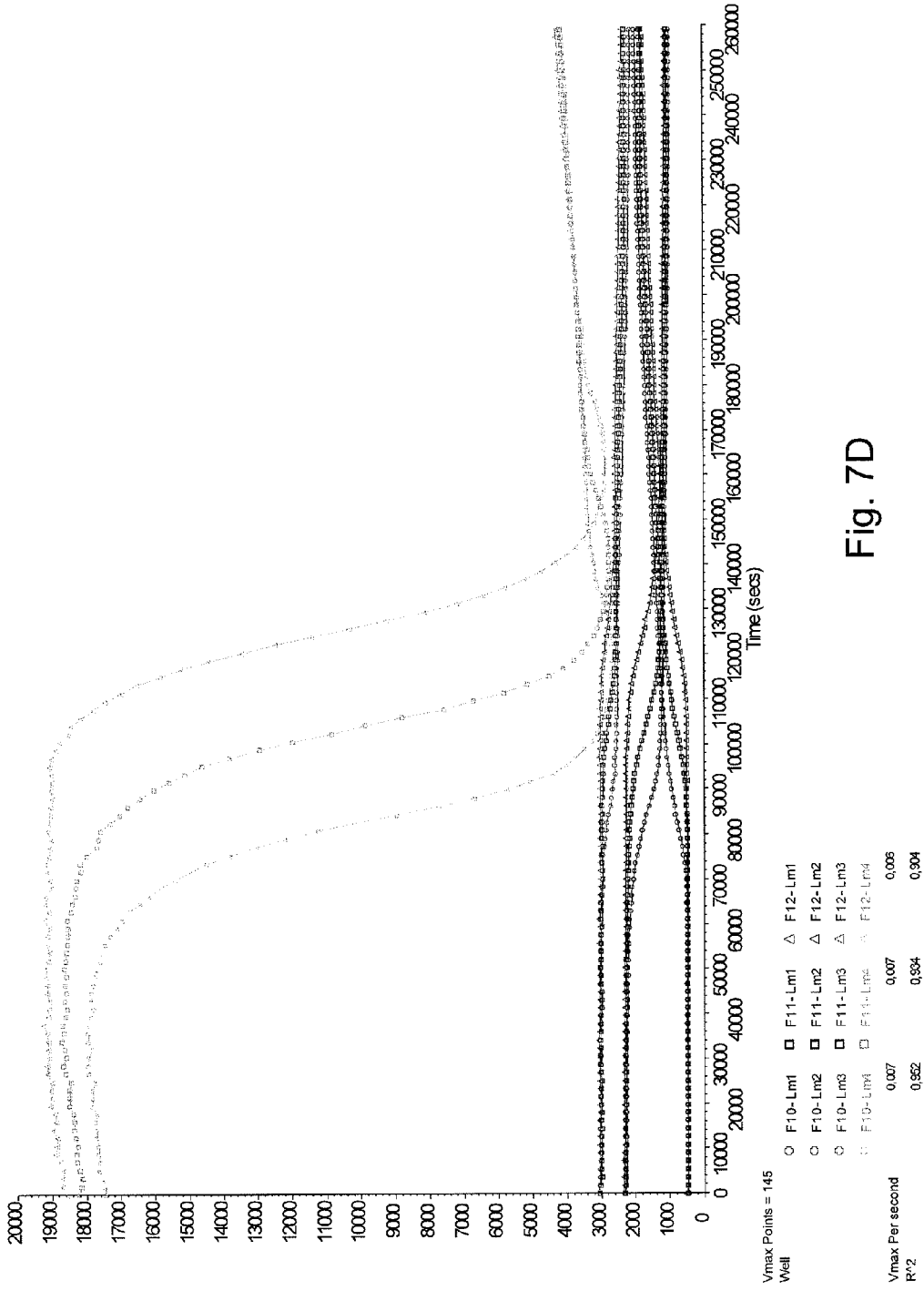
Figure 7E:
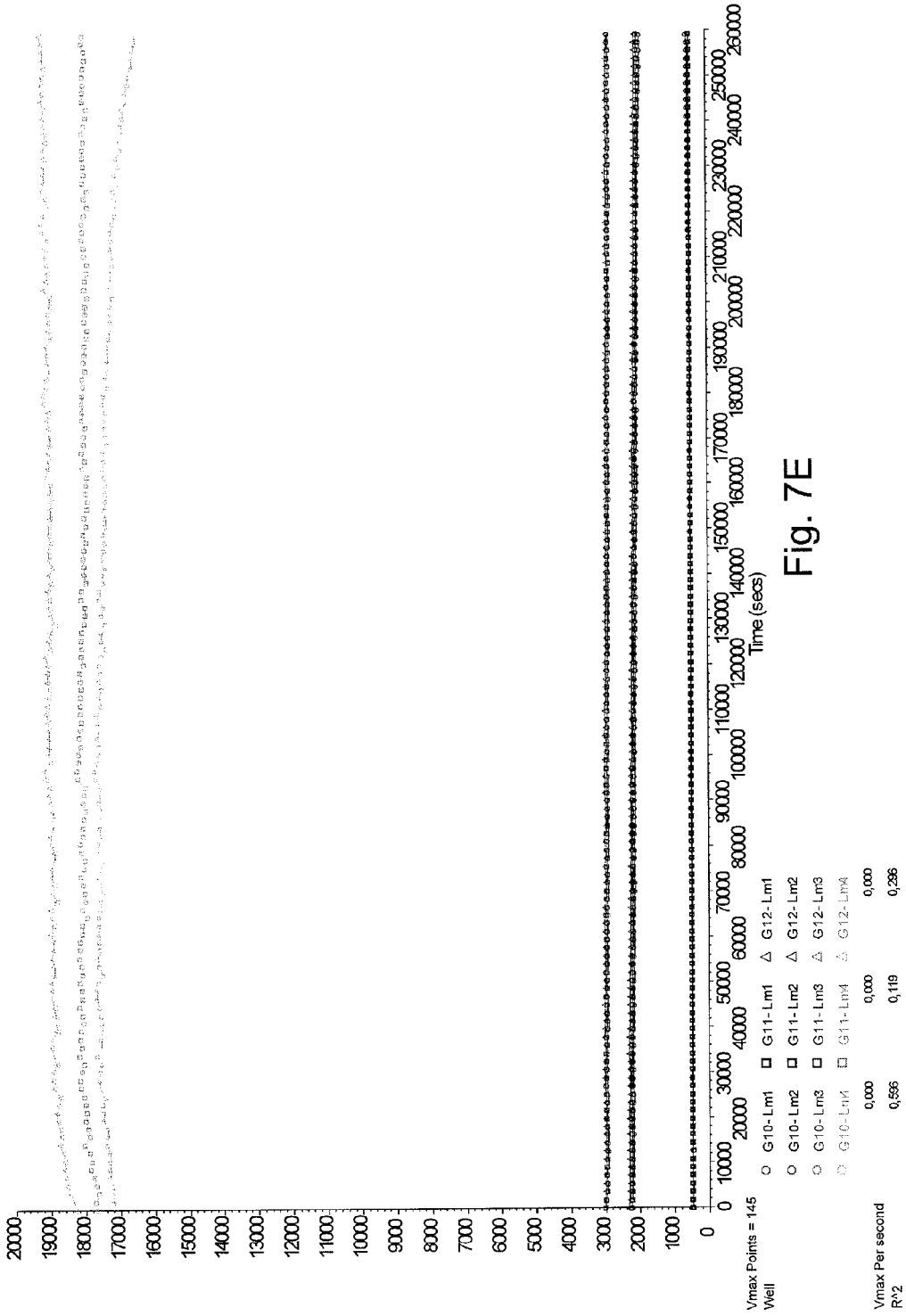
Figure 7F:
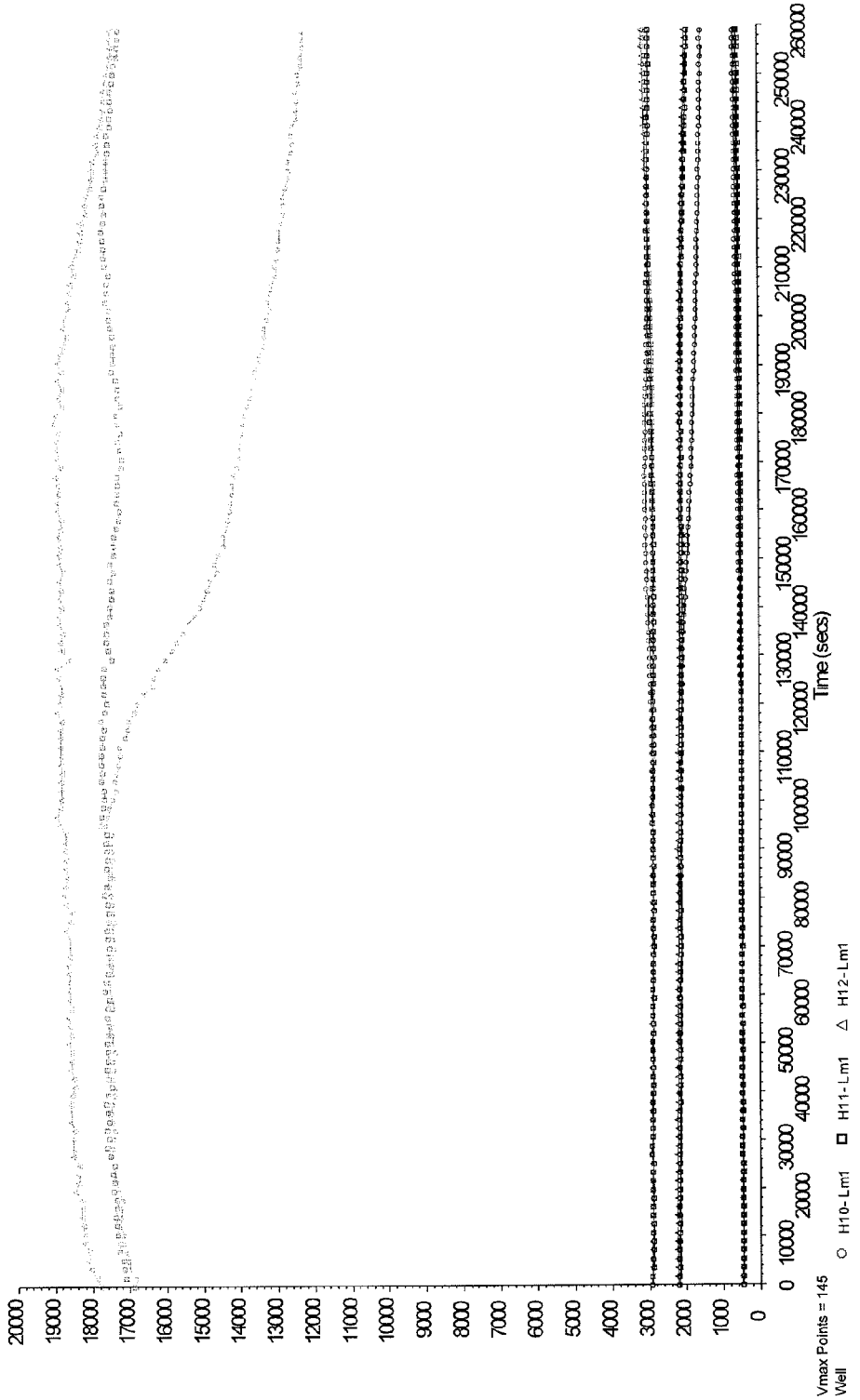
Figure 7G:
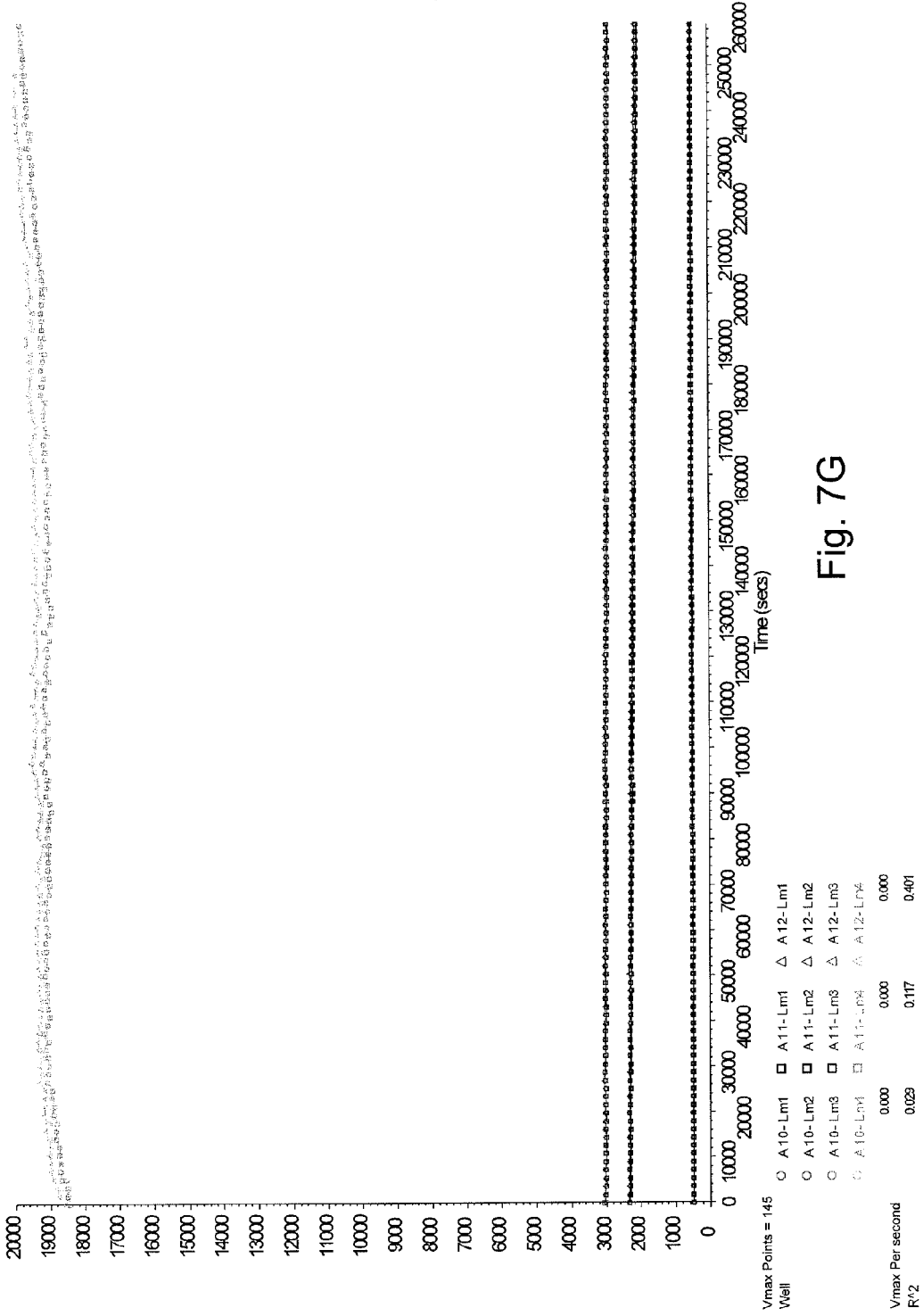

In all the cases a characteristic profile for the microorganisms is obtained on the channel enabling a drop in pH (HPTS or CF) to be measured, as well as on that enabling the metabolic activity to be measured (4-MU or Aldol). In particular, very atypical profiles are obtained in the case of P. aeruginosa, the signal linked to the use of HPTS increases whereas the pH drops (FIGS. 4B and 6B).

Figure 4D:
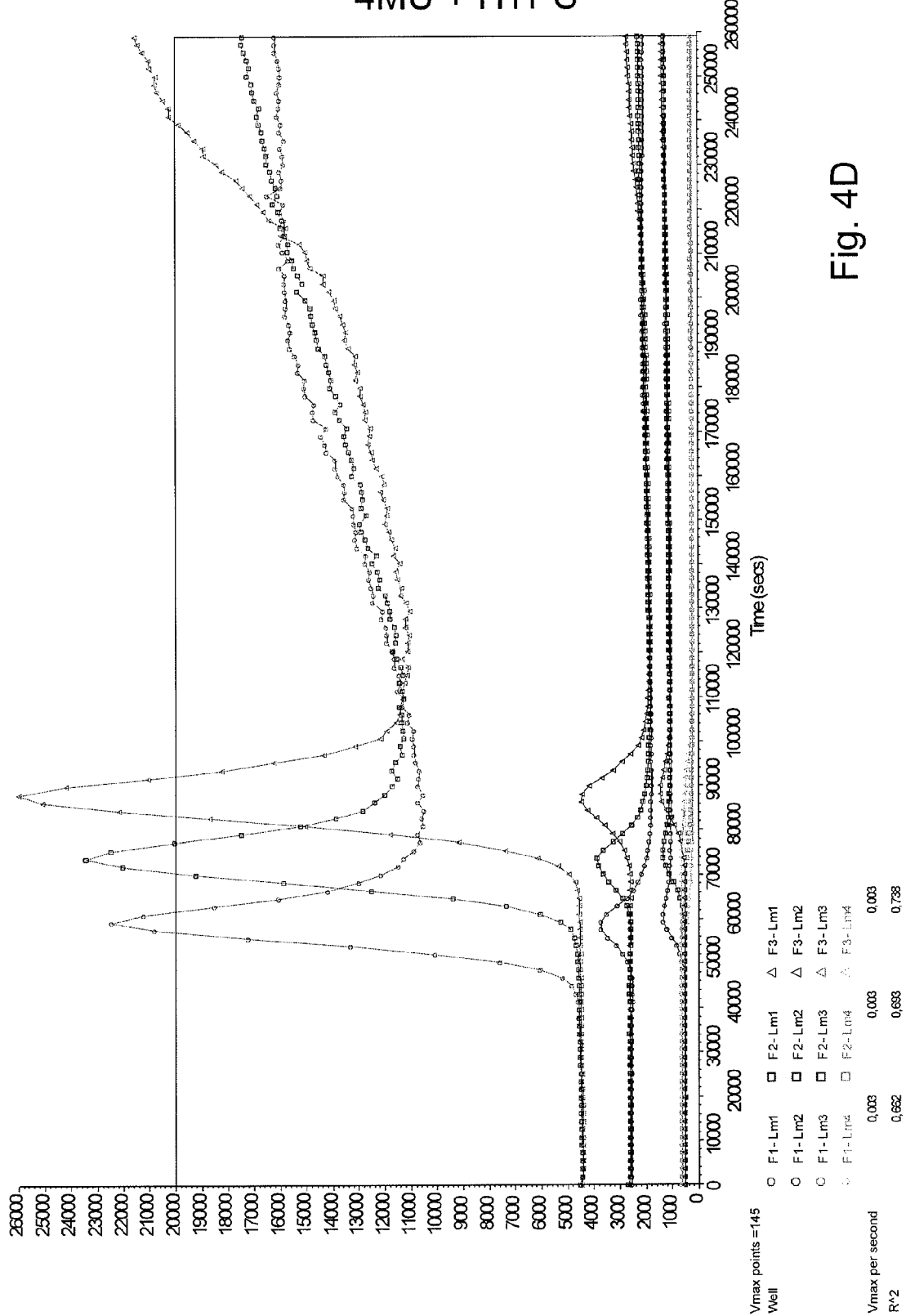
Figure 4E:
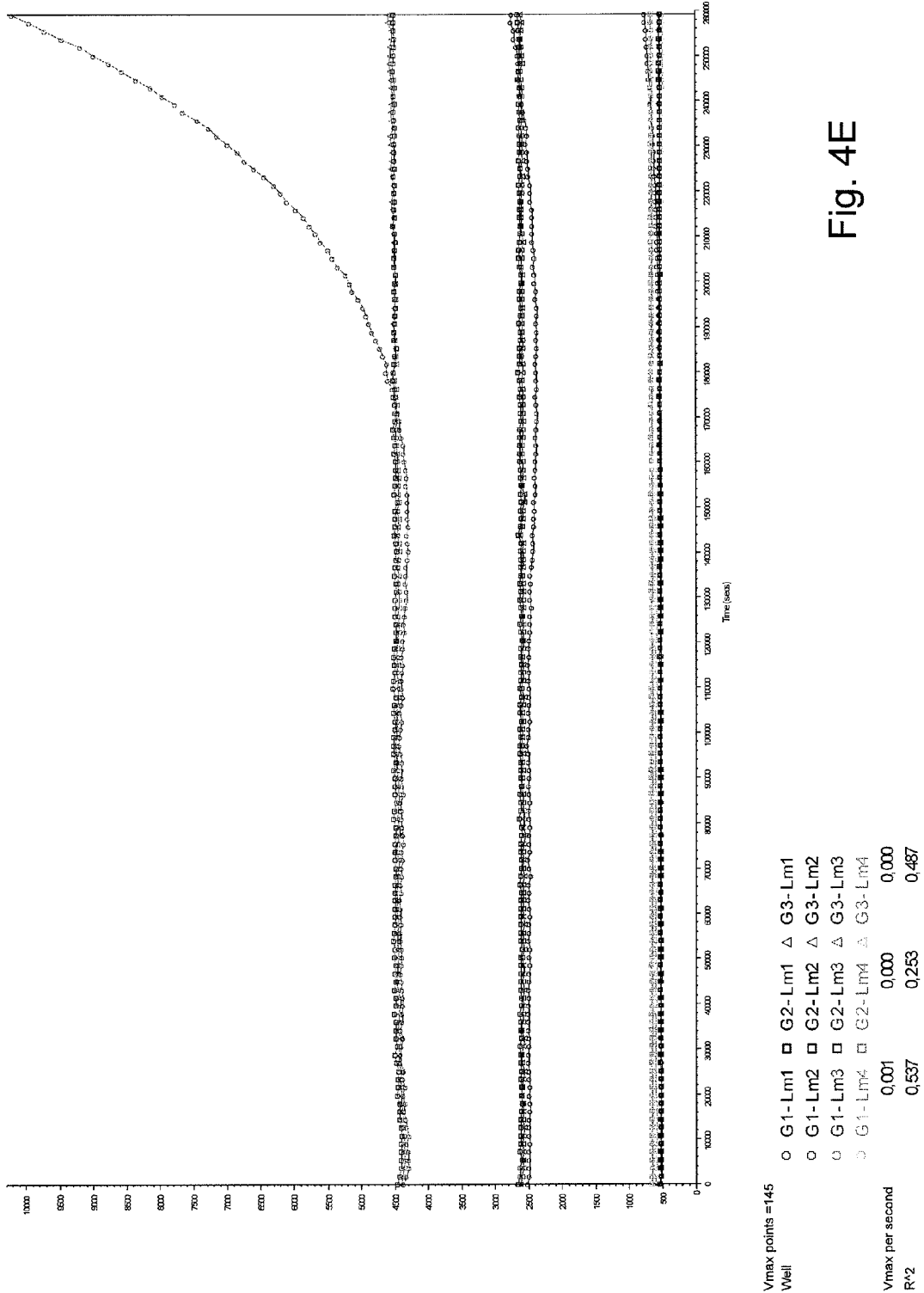
Figure 4F:
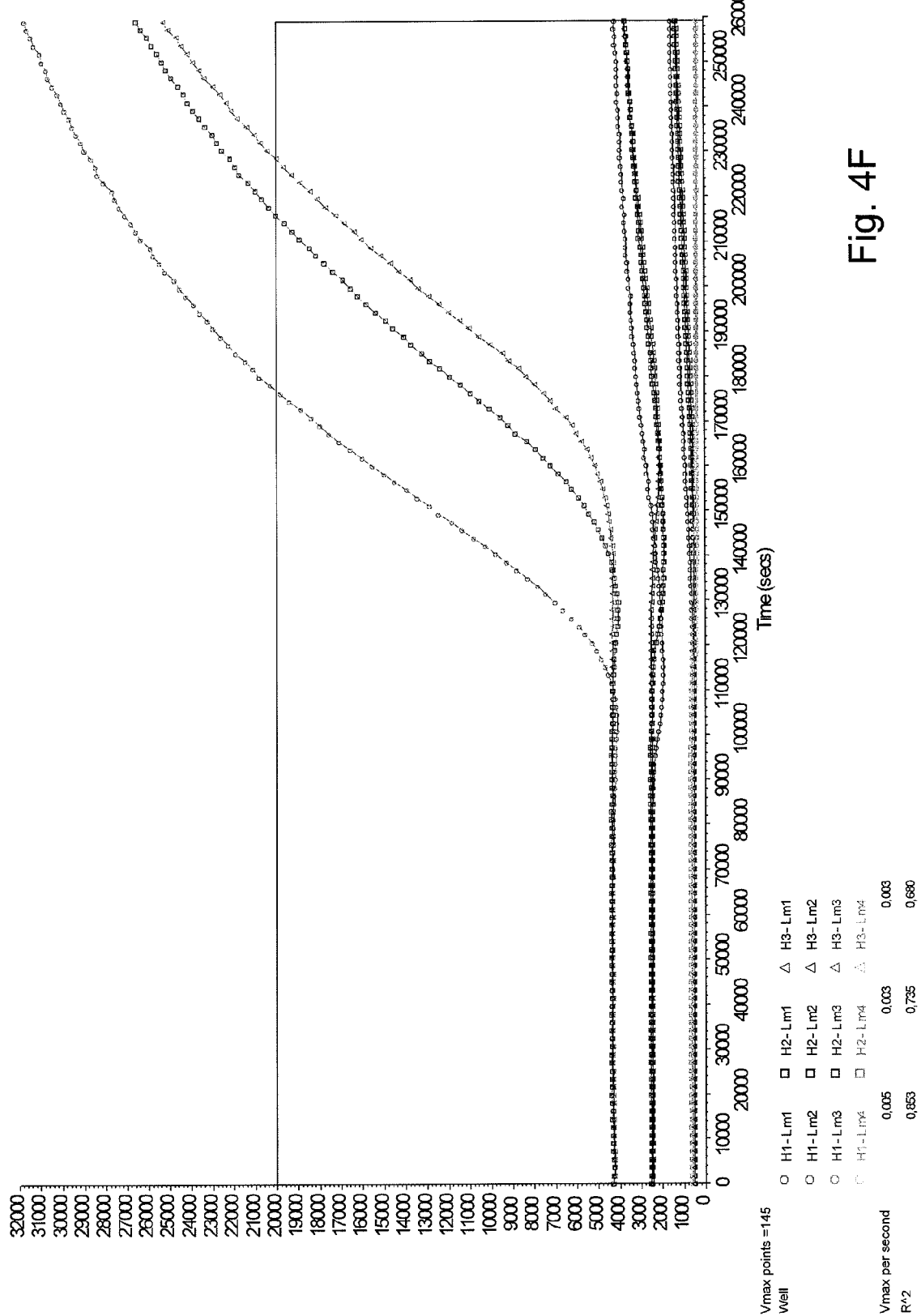
Figure 4G:
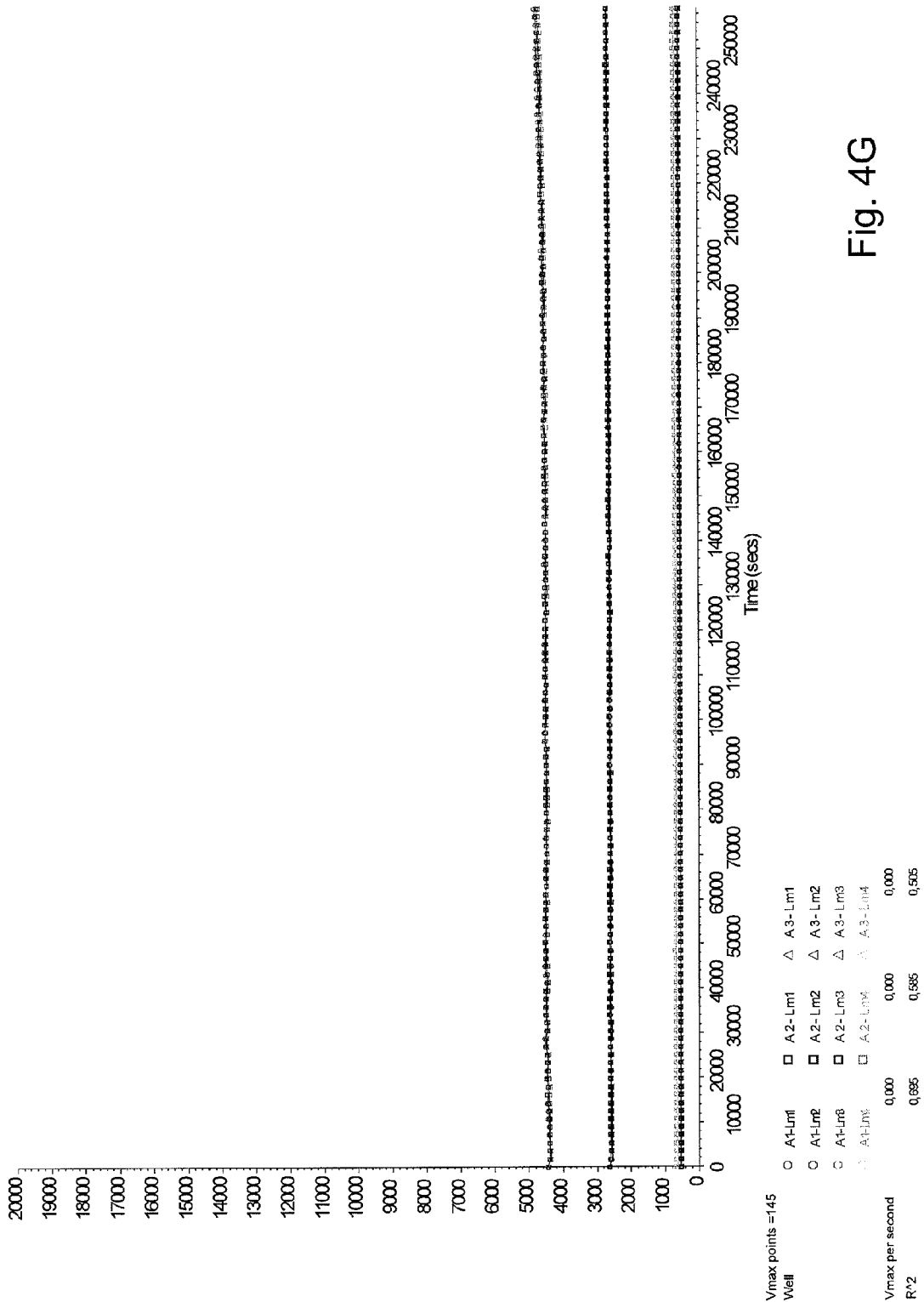
Figure 5A:
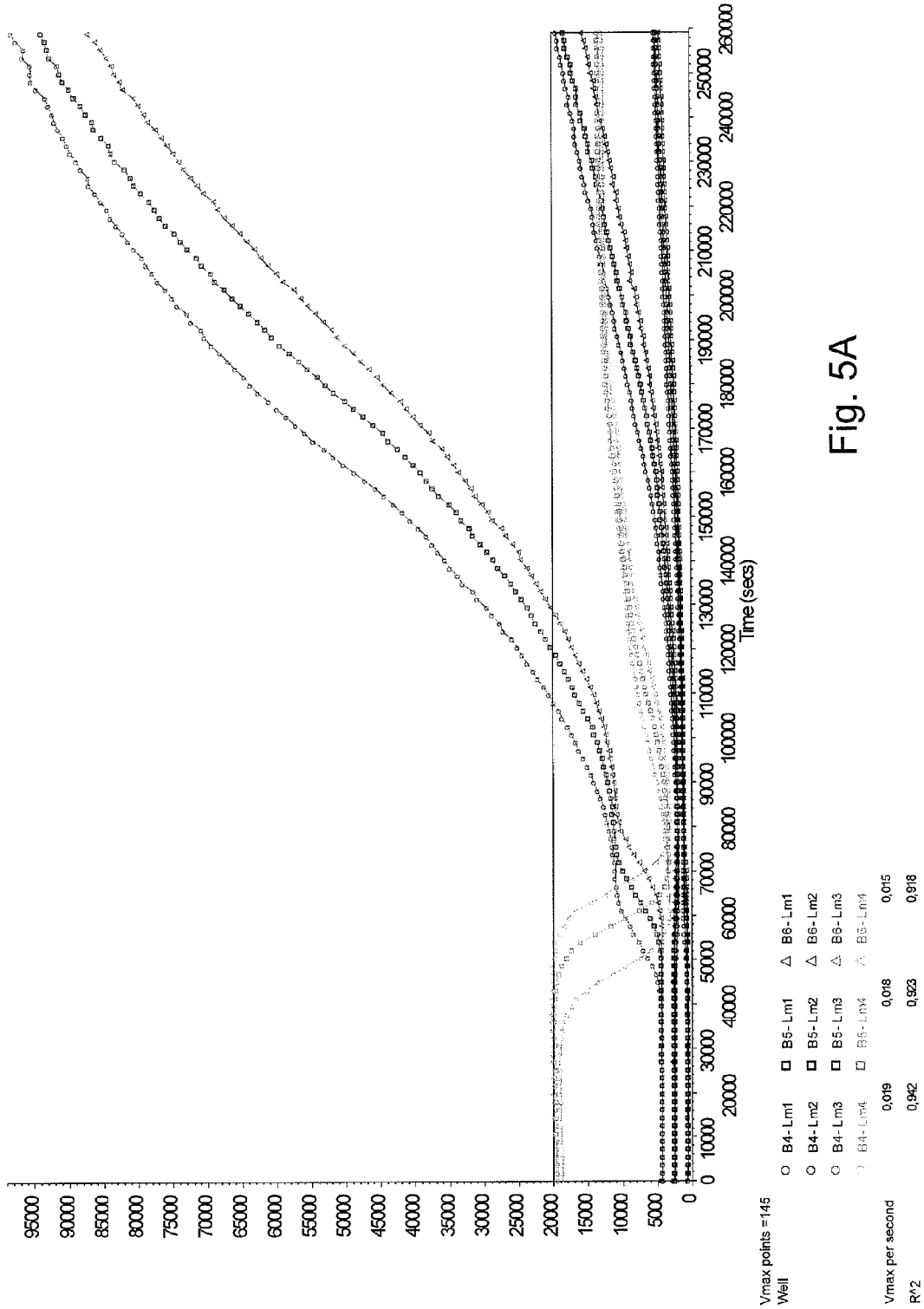
Figure 5B:
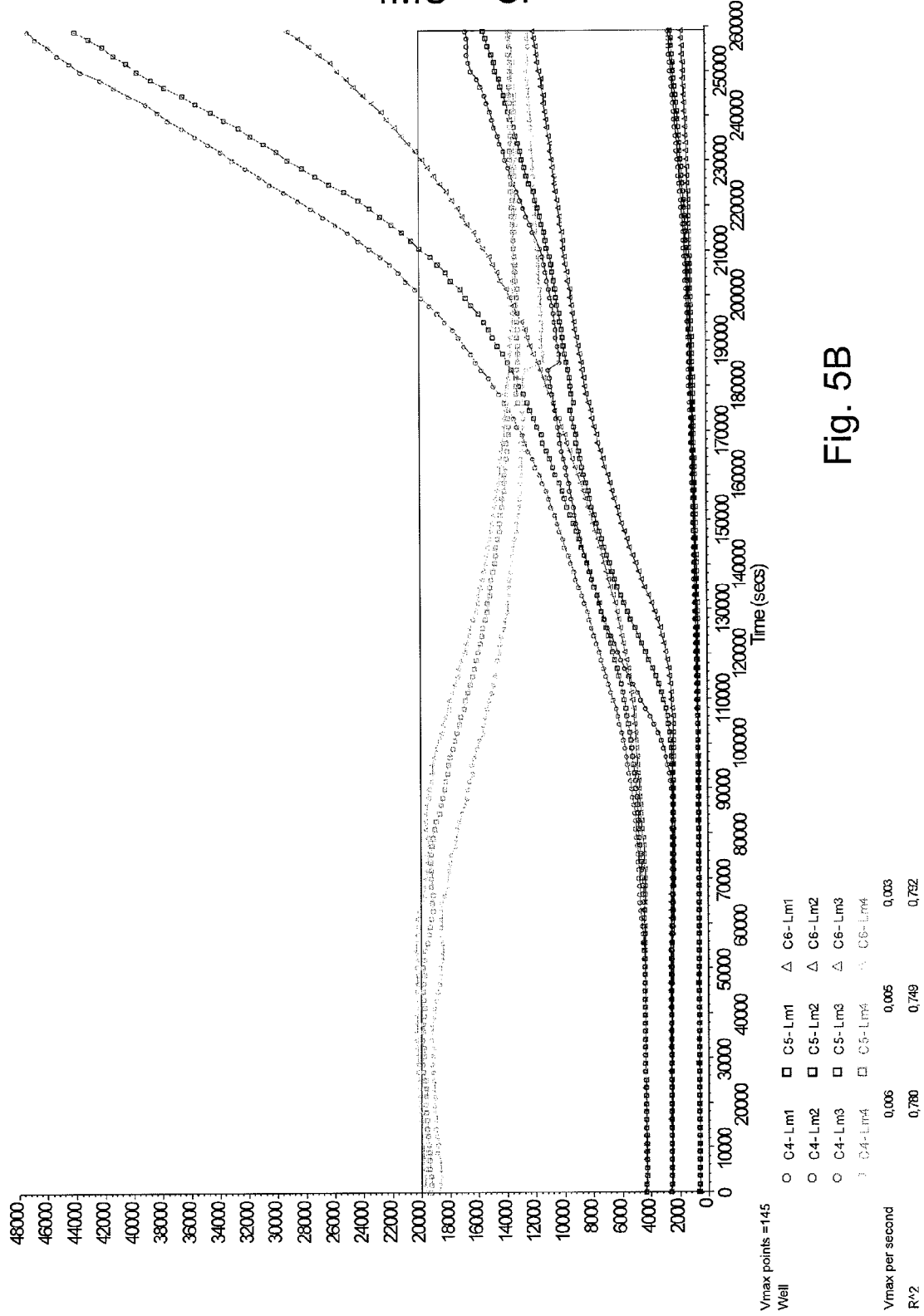
Figure 5C:
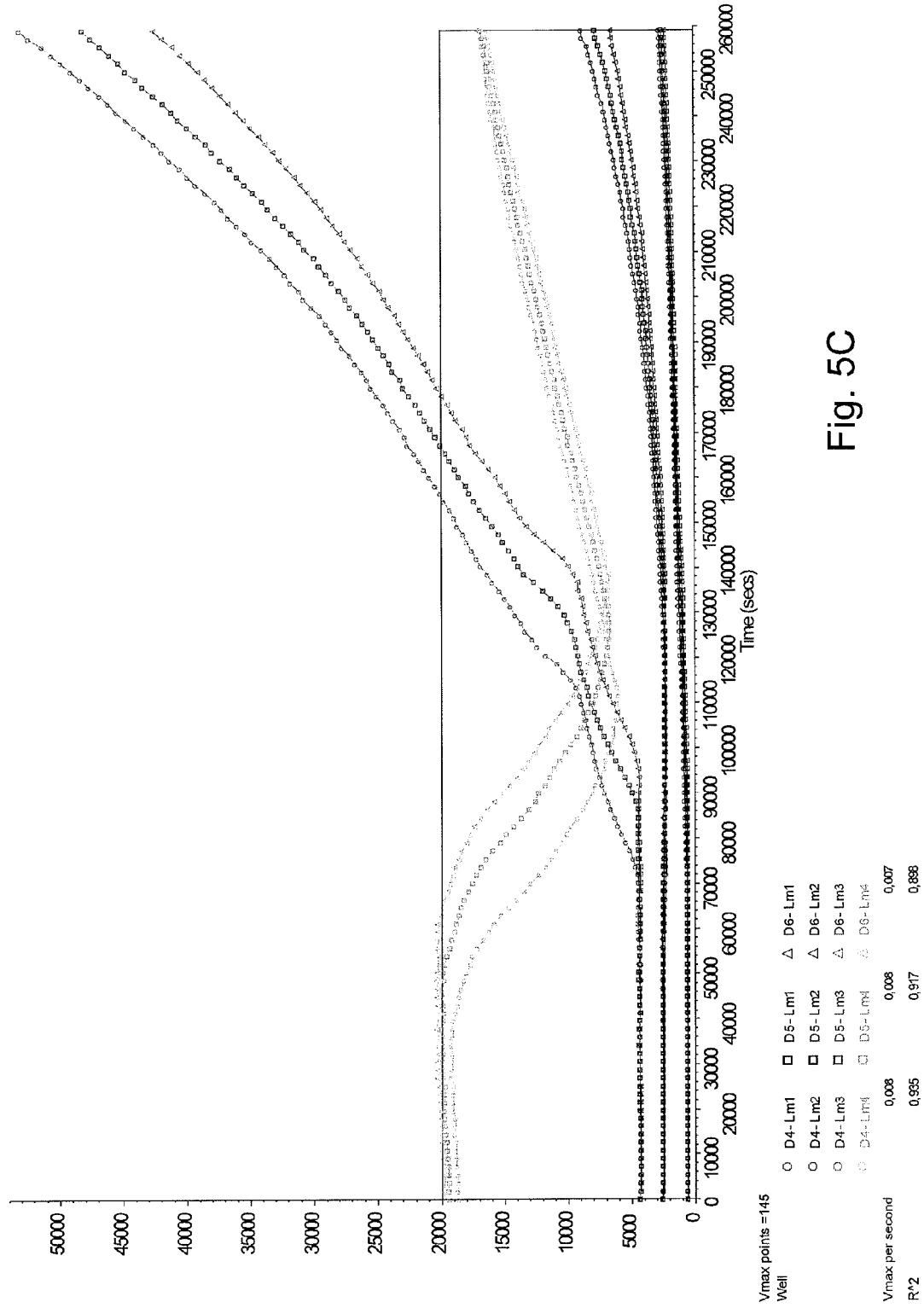
Figure 5D:
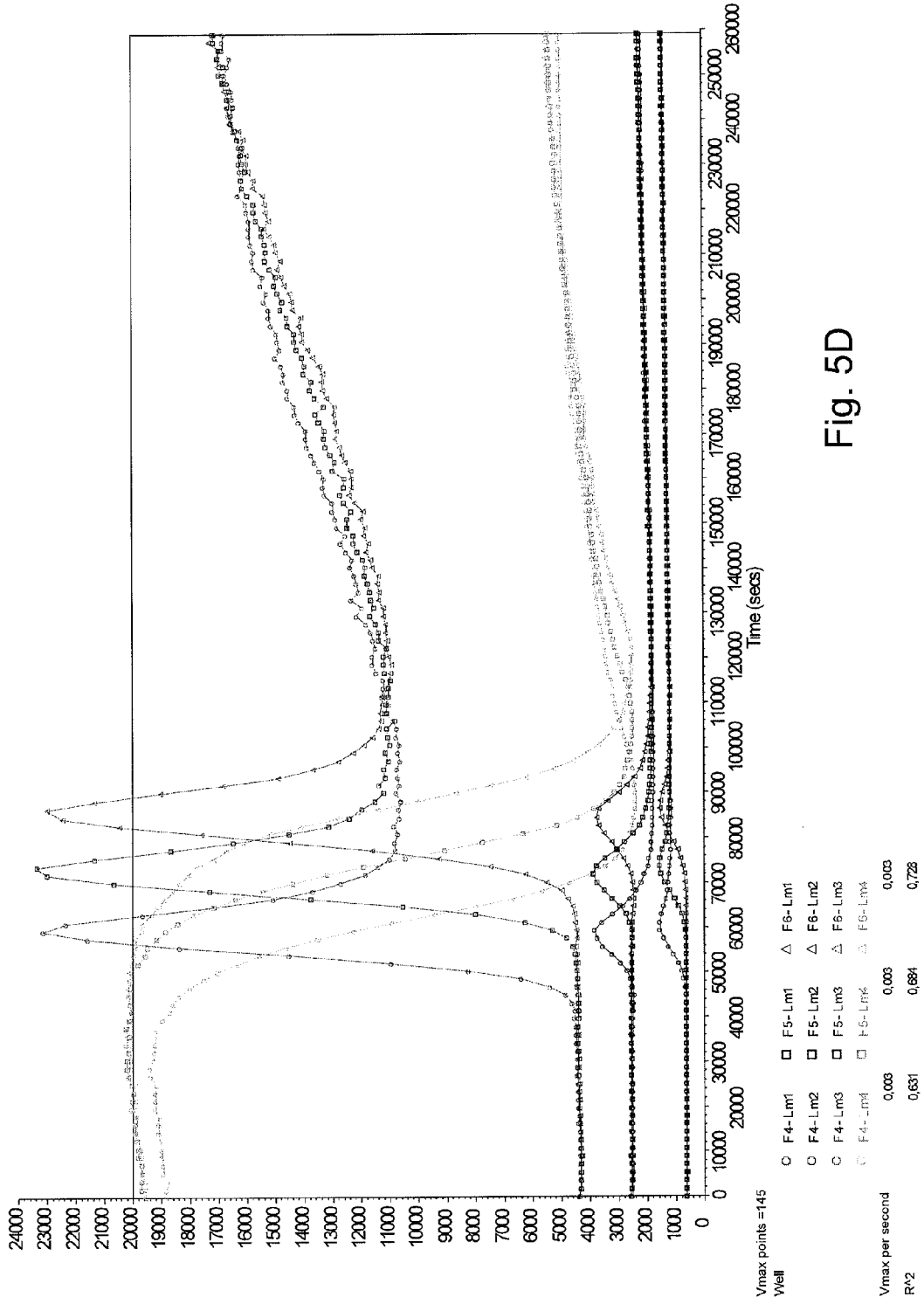
Figure 5E:
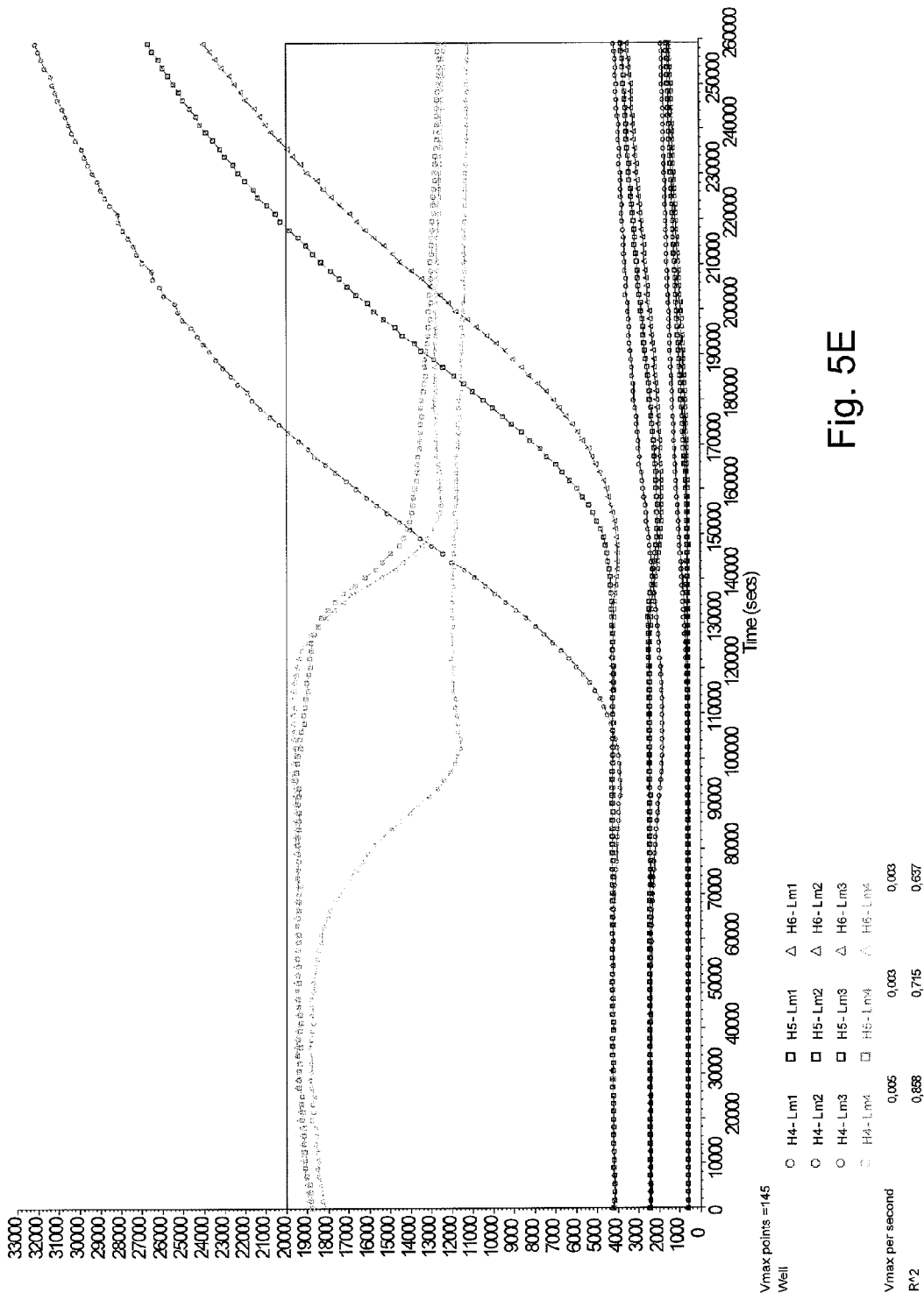
Figure 5F:
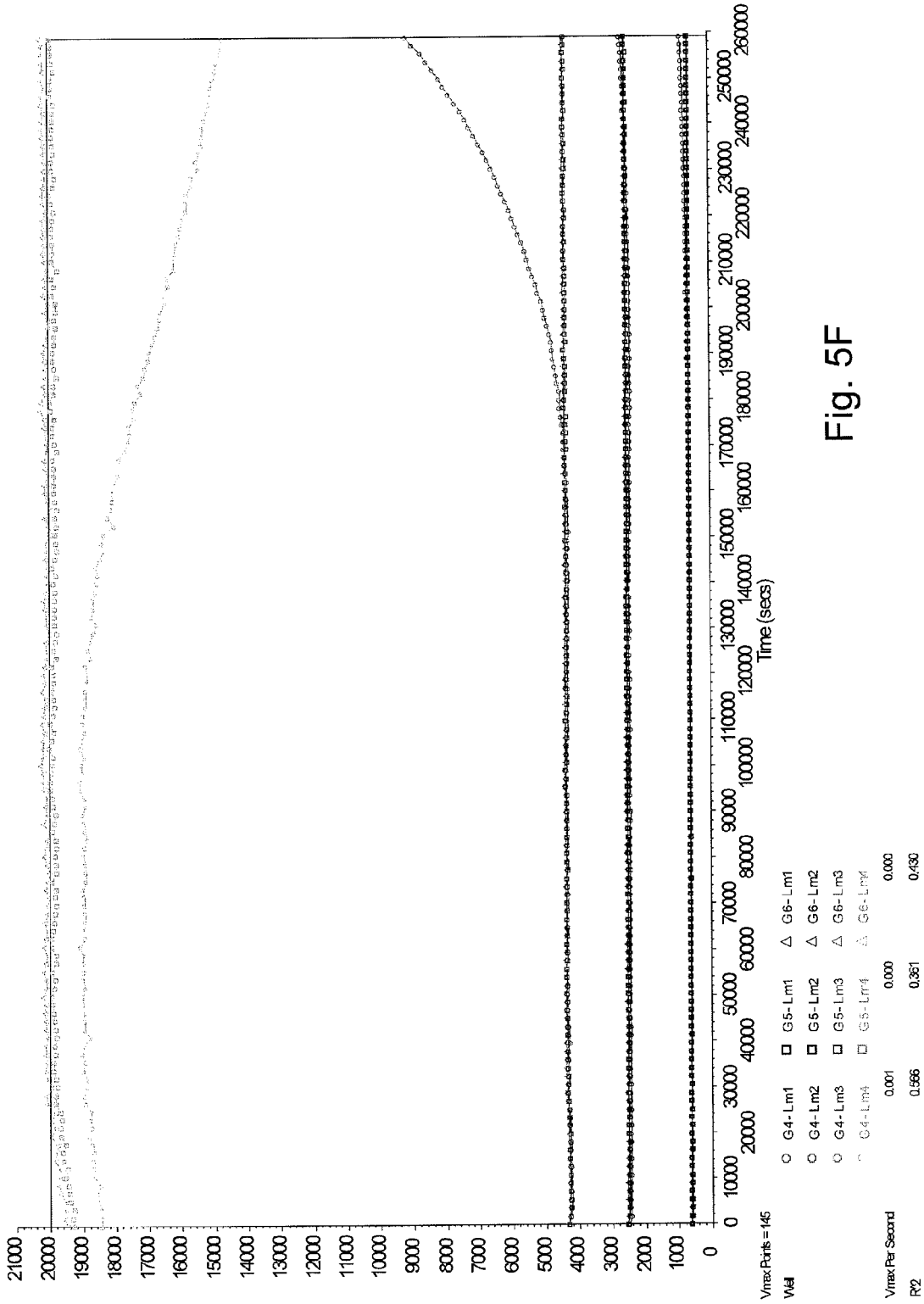
Figure 5G:
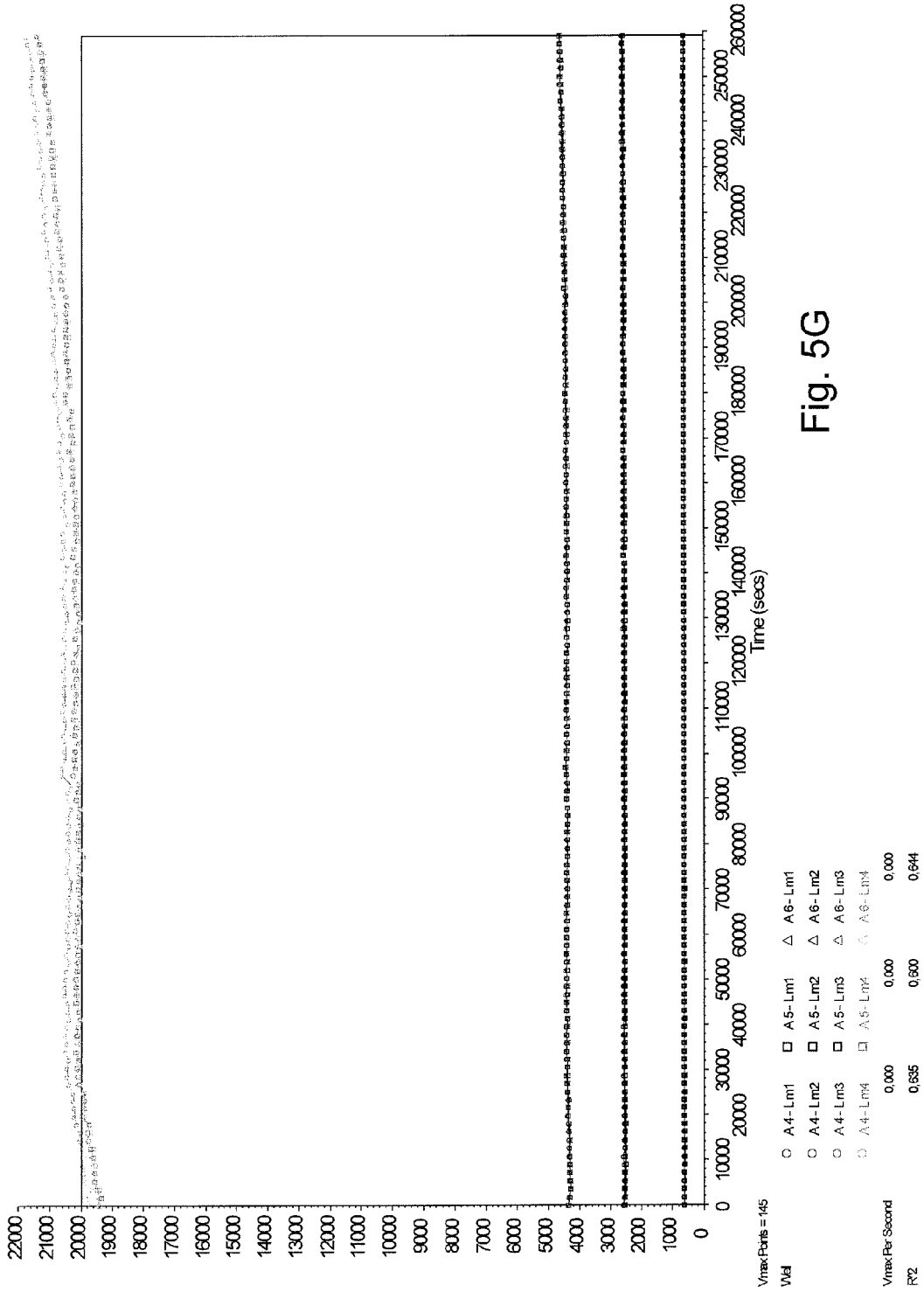

In a similar manner for S. aureus, the signal linked to the use of 4-MU forms a peak, then increases practically linearly (FIGS. 4D and 5D).

Profiles of pH drop that vary according to the strains (FIGS. 5 and 7) may be noted with regard to the use of carboxyfluorescein (CF).

The invention claimed is:

1. A growth medium for detecting the presence of microorganisms, comprising a nutritive support, in which are uniformly solubilized:
    at least one fluorogenic substrate that can be activated by at least one enzyme of a microorganism, wherein the fluorogenic substrate is a mixture of the following compounds:
    1-(2-benzoylphenyl)-6-chloro-1H-indol-3-yl-beta-glucopyranoside;
    1-(2-benzoylphenyl)-6-chloro-1H-indol-3-yl-beta-galactopyranoside;
    1-[2-(2,4-dimethoxybenzoyl)phenyl)]-1H-indol-3-yl-acetate; and
    1-[2-(2,4-dimethoxybenzoyl)phenyl]-1H-indol-3-yl-phosphate; and
    at least one fluorophore, of which the fluorescence is indicative of the pH of said growth medium, the fluorescence of said support itself being insensitive to the variations in pH of the growth medium and to the introduction of said microorganisms into the growth medium, wherein said at least one fluorophore and said at least one fluorogenic substrate are different compounds.

2. A growth medium according to claim 1, wherein said fluorophore, of which the fluorescence is indicative of the pH of the growth medium, is selected from the group consisting of 8-hydroxypyrene-1,3,6-trisulfonic acid (HPTS), a cyanine compound or one of its derivatives, and a fluorescein compound or one of its derivatives, salts or esters.

3. A growth medium according to claim 1, wherein said fluorophore, of which the fluorescence varies depending on the pH of the growth medium, is carboxyfluorescein or one of its salts or esters.

* * * * *